(12) United States Patent
Petisce et al.

(10) Patent No.: US 10,398,379 B2
(45) Date of Patent: Sep. 3, 2019

(54) SYSTEM FOR IMPROVED INTERPRETATION OF PHYSIOLOGICAL DATA AND PRESENTATION OF PHYSIOLOGICAL CONDITION MANAGEMENT INFORMATION

(71) Applicant: Becton, Dickinson and Company, Franklin Lakes, NJ (US)

(72) Inventors: James Petisce, Westford, MA (US); Ellen DiResta, Arlington, MA (US); Deborah Burns, Westford, MA (US); David Mason, Newburyport, MA (US); Sami Kanderian, Germantown, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 925 days.

(21) Appl. No.: 14/364,897

(22) PCT Filed: Dec. 14, 2012

(86) PCT No.: PCT/US2012/069766
§ 371 (c)(1),
(2) Date: Jun. 12, 2014

(87) PCT Pub. No.: WO2013/090731
PCT Pub. Date: Jun. 20, 2013

(65) Prior Publication Data
US 2014/0379273 A1 Dec. 25, 2014

Related U.S. Application Data

(60) Provisional application No. 61/576,309, filed on Dec. 15, 2011.

(51) Int. Cl.
*G01N 33/48* (2006.01)
*A61B 5/00* (2006.01)
(Continued)

(52) U.S. Cl.
CPC ............ *A61B 5/72* (2013.01); *A61B 5/14532* (2013.01); *A61B 5/7275* (2013.01); *A61B 5/742* (2013.01);
(Continued)

(58) Field of Classification Search
None
See application file for complete search history.

(56) References Cited

U.S. PATENT DOCUMENTS 4,731,726 A 3/1988 Allen, III
5,822,715 A 10/1998 Worthington et al.
(Continued)

FOREIGN PATENT DOCUMENTS

CN 101524267 A 9/2009
CN 101809947 A 8/2010
(Continued)

OTHER PUBLICATIONS

English Translation of Japanese Office Action dated Oct. 25, 2016 which issued in the corresponding Patent Application No. 2014-547489.
(Continued)

*Primary Examiner* — Larry D Riggs, II
(74) *Attorney, Agent, or Firm* — Dickinson Wright PLLC

(57) ABSTRACT

Systems, devices and methods for managing a physiological condition are configured to store predetermined output segments of content, analyze physiological data and other user information, and generate user-friendly information that provides an interpretation of the data (e.g., identifies selected data points, or determines pattern of physiological data over selected period(s)). An output segment management system with rules engine and method combines selected output segments to generate a presentation or message (e.g., with text, graphical, multimedia, video and/or
(Continued)

audio information). The resulting presentation or message provides user information such as an explanation of selected data with selected user information incorporated therein, and optional recommendations (e.g., suggested user actions based on a designated protocol such as a clinical protocol).

30 Claims, 18 Drawing Sheets

(51) Int. Cl.

| | |
|---|---|
| A61B 5/145 | (2006.01) |
| G08C 17/02 | (2006.01) |
| G16H 50/20 | (2018.01) |
| G16H 15/00 | (2018.01) |
| H04W 4/80 | (2018.01) |
| G06F 19/00 | (2018.01) |
| A61B 5/024 | (2006.01) |
| G16H 20/10 | (2018.01) |
| G16H 20/60 | (2018.01) |

(52) U.S. Cl.
CPC ............ *G06F 19/00* (2013.01); *G08C 17/02* (2013.01); *G16H 15/00* (2018.01); *G16H 50/20* (2018.01); *H04W 4/80* (2018.02); *A61B 5/002* (2013.01); *A61B 5/02438* (2013.01); *G06F 19/3456* (2013.01); *G16H 20/10* (2018.01); *G16H 20/60* (2018.01); *Y02A 90/26* (2018.01)

(56) References Cited

U.S. PATENT DOCUMENTS

| 6,122,536 | A | 9/2000 | Sun et al. | |
|---|---|---|---|---|
| 6,546,269 | B1 | 4/2003 | Kurnik | |
| 6,882,940 | B2 | 4/2005 | Potts et al. | |
| 7,022,072 | B2 | 4/2006 | Fox et al. | |
| 7,885,697 | B2 | 2/2011 | Brister et al. | |
| 2003/0036683 | A1 | 2/2003 | Kehr et al. | |
| 2003/0167185 | A1* | 9/2003 | Gordon | G06F 17/30893 705/2 |
| 2004/0015132 | A1* | 1/2004 | Brown | A61B 5/0002 604/131 |
| 2005/0088357 | A1 | 4/2005 | Hess et al. | |
| 2005/0209515 | A1 | 9/2005 | Hockersmith et al. | |
| 2007/0048691 | A1* | 3/2007 | Brown | A61B 5/044 434/127 |
| 2007/0253021 | A1 | 11/2007 | Mehta et al. | |
| 2008/0318624 | A1 | 12/2008 | Hedtke et al. | |
| 2009/0034591 | A1* | 2/2009 | Julian | H04W 4/206 375/220 |
| 2009/0043361 | A1 | 2/2009 | Baumgartner et al. | |
| 2009/0054737 | A1 | 2/2009 | Magar et al. | |
| 2009/0063402 | A1 | 3/2009 | Hayter | |
| 2010/0075353 | A1* | 3/2010 | Heaton | A61B 5/0002 435/14 |
| 2010/0088120 | A1 | 4/2010 | Gonzalvo | |
| 2011/0021898 | A1 | 1/2011 | Wei et al. | |
| 2011/0193704 | A1 | 8/2011 | Harper et al. | |
| 2011/0237918 | A1 | 9/2011 | Wagner et al. | |
| 2014/0114161 | A1 | 4/2014 | Kamath et al. | |

FOREIGN PATENT DOCUMENTS

| EP | 1770900 A1 | 4/2007 |
|---|---|---|
| JP | 2001-515620 | 9/2001 |
| JP | 2003-51891 | 2/2003 |
| JP | 2005-525149 | 8/2005 |
| JP | 2005328924 A | 12/2005 |
| JP | 2006-014076 A | 1/2006 |
| JP | 2007-529959 A | 10/2007 |
| JP | 2008-229331 | 10/2008 |
| JP | 2009-099083 A | 5/2009 |
| JP | 2010-530784 | 9/2010 |
| JP | 201164597 A | 3/2011 |
| JP | 2011147784 A | 8/2011 |
| WO | 00/49797 A | 8/2000 |
| WO | WO 2011/025549 A1 | 3/2011 |

OTHER PUBLICATIONS

Chinese Office Action issued by Chinese Patent Office, dated Oct. 10, 2015 that issued in counterpart Patent Applicaiton No. 201280067587.7, incl. English translation.
Japanese Office Action dated Jul. 10, 2018, which issued in the corresponding counterpart Japanese Patent Application No. 2017-227242, including English translation.
Japanese Office Action dated Sep. 25, 2018, which issued in the corresponding counterpart Japanese Patent Application No. 2017-212965, including English translation.
Japanese Office Action dated Apr. 2, 2019, which issued in the counterpart Patent Application No. 2017-227242, including English translation.

\* cited by examiner

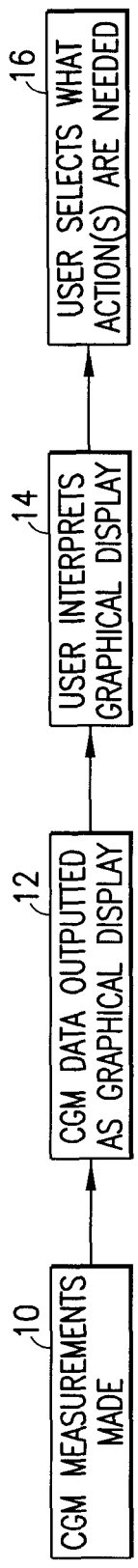

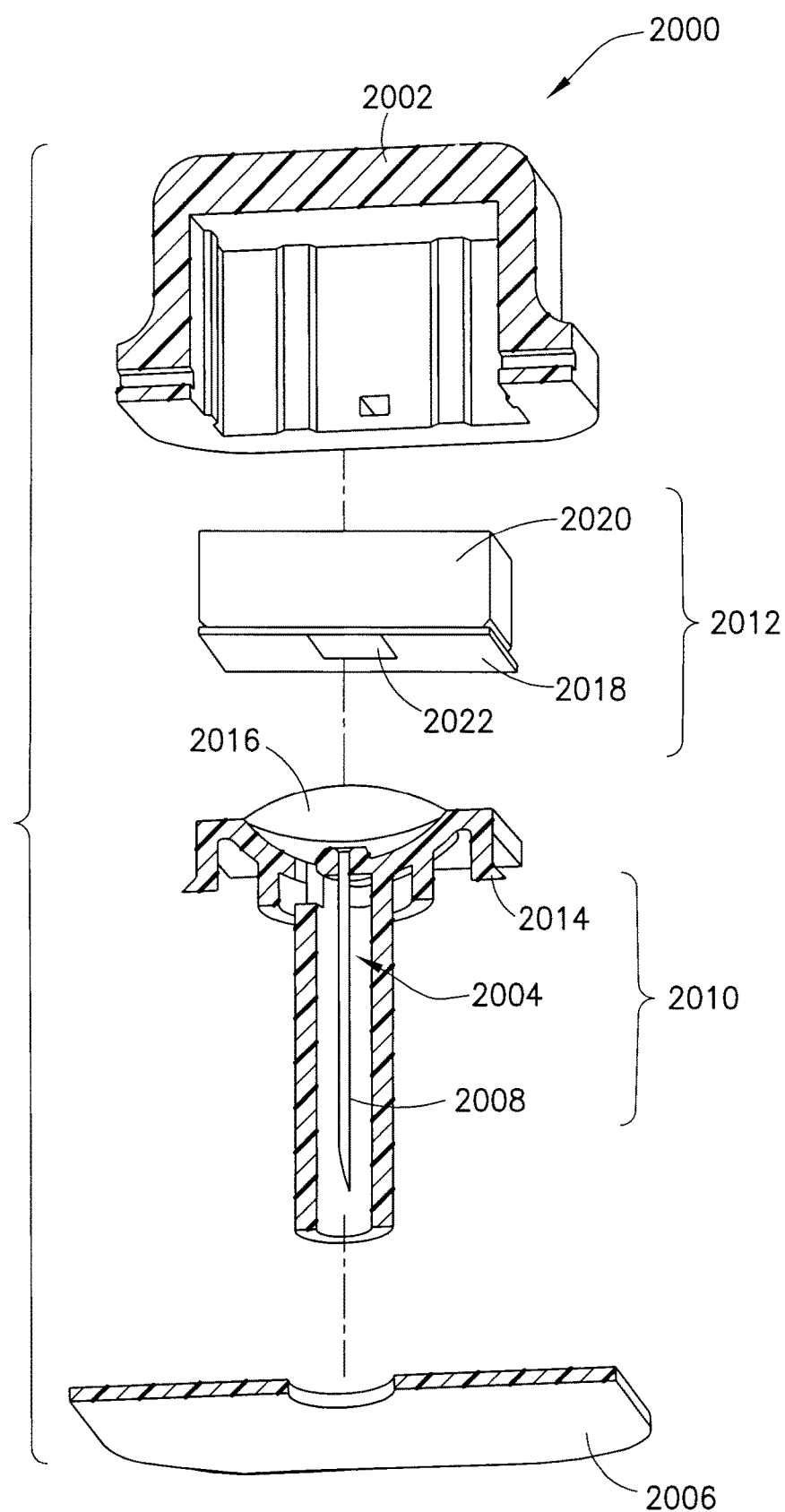

SYSTEM FOR IMPROVED INTERPRETATION OF PHYSIOLOGICAL DATA AND PRESENTATION OF PHYSIOLOGICAL CONDITION MANAGEMENT INFORMATION

BACKGROUND OF THE INVENTION

Field of the Invention

The present invention relates generally to apparatuses, methods and systems for sensing or measuring physiological data, analyzing the data, and outputting user-friendly information providing an interpretation of the data for improved management of one or more physiological conditions.

Description of Related Art

With reference to blocks 10 and 12 of FIG. 1, continuous glucose monitors (CGMs) provide a user such as a patient, clinician or caregiver with a patient's glucose measurements throughout the day (e.g., a glucose measurement every one to five minutes 24 hours per day). Accordingly, the quantity of data provided to the CGM user is tremendous. This data is typically presented to the end user as a graphical display wherein the glucose values measured by the CGM are plotted as a function of time of day. Examples of such data are the graphical display of blood glucose measurements over a 14 hour period shown in FIGS. 20A and 20B of U.S. Pat. No. 7,905,833, and the tabular display shown in FIG. 10 of U.S. Pat. No. 7,890,295 of a continuous electrical current signal (ISIG) (i.e., table column E) measured at various times (i.e., table column D) by a glucose sensor.

The user can usually set what time period to view his measured data (e.g., the x-axis in FIG. 2 of U.S. Pat. No. 6,882,940), thereby adjusting the time period of viewable measured data to one hour, or 24 hours, or 72 hours, for example. The user can also set alarm levels to generate audible alarms, for example, when a measured glucose value is below a low glucose alarm level or above a high glucose alarm level.

Nonetheless, the graphical, tabular or numerical display of measured physiological data (e.g., blood glucose measurements from a CGM) is difficult and, in many cases, cumbersome for a user to interpret and decide what action(s) is needed to manage a physiological condition, as depicted in blocks 14 and 16 of FIG. 1. Further, even relatively simple alphanumeric displays such as the device screens depicted in FIGS. 6A-6D of U.S. Pat. No. 7,022,072 can be difficult for a user to interpret, that is, specific outlier data (e.g., measured values outside a threshold) are merely reported, but no user-friendly information is provided to indicate, for example, what the outlier data signifies about the user's monitored physiological condition or how such data can be mitigated. In other words, a need exists for a device that interprets measured data to provide information to the user in a convenient and more easily comprehended manner such as a video display on a user device that provides a virtual coach (e.g., a video and/or graphical and/or audible presentation with audio and/or visual output) that provides user-friendly interpretation of specific outlier data, for example, and an explanation of why the outlier data occurred and, optionally, suggestions for user actions to mitigate the effects of the outlier data such as in the context of a monitored physiological condition (e.g., an automatically generated output that states "Hypoglycemic events were measured during this time on 3 of the last 5 days. A mid-morning snack can help prevent or lessen the impact of future AM hypoglycemic events.").

In existing physiological condition monitors or measuring devices, measured physiological data is merely presented as data, leaving the user with the difficult task of interpreting what the data means. Even with availability of alarms to advise a user of measured data being outside a selected threshold, a multitude of other data may need to be considered and interpreted to determine a course of action, if any, that should be taken in response to that alarm. A need exists for a physiological condition measuring and/or monitoring device that automatically analyzes and interprets measured data, along with any other user data that may impact a physiological condition, to select and output information regarding the measured data that is determined to be what the user needs to know (e.g., selected outliers or patterns and why they likely occurred and/or actions to offset or correct the outliers or patterns, or prospectively determined data and/or actions to prevent predicted outlier data sets).

The T1D Exchange Clinical Registry currently enrolls approximately 15,000 persons with Type 1 Diabetes across approximately 65 diabetes centers in the United States from whom to collect and store data to create a biobanking dataset and Type 1 diabetes portal.

According to downloading trend information available via this portal, less than 5% of these persons download data (e.g., their blood glucose values collected from their monitoring devices) on a weekly basis. Only about 12% of these persons download their data on a monthly basis. An astonishing 88% of these participants never view their downloaded data. The majority of T1D Exchange participants are reluctant to download and view their data because it takes too much time and they do not receive meaningful information from the data. T1D Exchange participants find the data simply too difficult to interpret and use in a meaningful manner and prefer to manage their diabetes test by test, injection by injection, relying instead on their healthcare provider to advise them when they need to make significant changes to their diabetes management regimens.

The EV1000 clinical platform from Edwards Lifesciences further illustrates problems with current methods of presenting physiological status of a patient in a clinical setting. Although the EV1000 clinical platform is intended to be the state of the art in providing patient physiological data in a more intuitive and meaningful way (e.g., in an operating room (OR) or in an intensive care unit (ICU)), the monitored data is merely graphically represented without any interpretation and determination of what information a clinician needs to know about the monitored data or recommended course of action or display of clinically acceptable courses of actions based on the monitored data. The display of more monitored data, even if done in an attractive graphical manner, does not necessarily make that data useful to a healthcare provider, particularly in a critical care setting such as an OR or ICU. Some form of interpretation of that data is often needed, and the cognitive load on the practitioner actually increases with added data.

A need therefore exists, in both ambulatory and non-ambulatory healthcare settings, for physiological condition monitoring devices that remove cognitive load/burden from the user when interpreting the data and deciding on a course of action. That is, a need exists for a monitoring method and/or apparatus that takes digital output from a device (e.g., downloaded data) and interprets the data for the user to provide the user with useful information (e.g., a determination of what information the user needs to know about retrospective data or a prospective data analysis).

SUMMARY OF THE INVENTION

The above and other problems are overcome, and additional advantages are realized by illustrative embodiments of the present invention.

In accordance with illustrative aspects of the present invention, a method and system are provided to facilitate managing a physiological condition by measuring one or more physiological data parameters, interpreting the data by identifying and selecting physiological patterns or data points to be annunciated to a user, and outputting the selected information and optionally a recommendation and/or course of action in an easy to comprehend and user-friendly manner.

Apparatuses, methods and systems are provided in accordance with illustrative embodiments of the present invention for sensing or measuring physiological data, analyzing the data, and outputting user-friendly information to provide an interpretation of the data for improved management of one or more physiological conditions. To facilitate analyzing and interpreting data, users provide configuration information (e.g., personal data, clinician data, healthcare setting, intended end user) that affects thresholds and rules employed by a rules engine, for example. Users can also configure different types of outputted information such as: selected summaries or patterns of data or data point(s), and/or selected recommendations or instructions for user actions; frequency and types of alerts or reminders; and output modalities (e.g., format such as audio, video, alphanumeric, graphical, and delivery method such as display, audio message, text message and/or video provided via user device, medical monitoring device, television, personal computer, cellular phone or other portable user device, vehicle user interface, and so on). One modality for outputting user-friendly information providing interpretation of physiological data is streaming videos (e.g., video segments selected based on the physiological data selected for output and user configuration data) that provide user with a selected summary of or pattern determined to exist in the physiological data and/or instructions for specific user actions to manage a physiological condition in view of the summary or pattern.

In accordance with illustrative embodiments of the present invention, a method of generating physiological condition information is provided that comprises: receiving physiological data corresponding to a user; storing the physiological data and user information in a memory device, the user information selected from the group consisting of physiological data thresholds, meal times, exercise times, age, weight, medication, amounts and times of medication administration, heart rate, body temperature, and food intake information; analyzing, via a processing device, the physiological data to determine at least one of a selected data point, and a pattern of the physiological data over at least one selected period of time, using a designated protocol for managing the physiological condition and at least one of the user information; and generating, via the processing device, a presentation of physiological condition information that comprises a video, the video presenting an explanation of the determined data point or pattern that includes at least one of values selected from among the stored physiological data and the stored user information that contributed to the determined data point or pattern, and values derived from at least one of the stored physiological data and the stored user information that contributed to the determined data point or pattern.

In accordance with further illustrative embodiments of the present invention, a plurality of output segments are stored in the memory device that are predetermined and stored independently of the received physiological data. The output segments are at least one of audio segments and video segments, and the generating comprises selecting and combining selected ones of the output segments to create a video or other presentation (e.g., video recordings, audio recordings and graphical representations of a person or character presenting at least part of the presentation). The presentation can comprise at least one of an audio output, a graphical output, an audiovisual output, and an alphanumeric output. The output segments are recordings of user instructions for performing at least part of a physiological condition management action, and the analyzing comprises selecting one of a plurality of physiological condition management actions. Combining selected ones of the output segments can comprise at least one of concatenating the selected ones of the output segments, overlaying the selected ones of the output segments, splicing the selected ones of the output segments into one another or into a separate stream, and outputting the selected ones of the output segments in respective positions in an output display screen. The generating can comprise at least one of inserting the values among the combined output segments, simultaneously displaying the values in at least one of the combined segments, and combining the values with the combined output segments.

In accordance illustrative embodiments of the present invention, a method of generating physiological condition information is provided that comprises: storing in a memory device a plurality of output segments that are predetermined and based on a designated protocol for managing the physiological condition, the stored output segments being at least one of audio, video, graphical, alphanumeric and audiovisual content; receiving physiological data corresponding to a user; storing the physiological data and user information in the memory device, the user information selected from the group consisting of physiological data thresholds, meal times, exercise times, age, weight, medication, amounts and times of medication administration, heart rate, body temperature, and food intake information; analyzing, via a processing device, the physiological data to determine at least one of a selected data point from the physiological data and a pattern of the physiological data over at least one selected period of time using at least one of the user information and protocol data for managing the physiological condition; and generating, via the processing device, a presentation of physiological condition information that is selected based on the designated protocol and comprises an explanation of the determined pattern or selected data point based on the designated protocol by combining selected ones of the output segments to create the presentation. In accordance further illustrative embodiments of the preset invention, the method of generating physiological condition information can further comprise inserting values among the combined output segments, the values being at least one of values selected from among the stored physiological data and the stored user information that contributed to the determined pattern, and values derived from at least one of the stored physiological data and the stored user information that contributed to the determined pattern. In addition, the predetermined output segments are at least parts of instructions for user actions to perform at least part of the designated protocol for managing a physiological condition in a user having the determined pattern or selected data point.

In accordance with illustrative embodiments of the present invention, the method can be performed via a processing device comprising or having access to a rules engine that determines the physiological condition information selected for the presentation based on the designated protocol.

In accordance with illustrative embodiments of the present invention, the physiological condition and the physiological data are related to glycemic control. The physiological data are measured subcutaneously or intravenously.

In accordance with illustrative embodiments of the present invention, receiving the physiological data comprises: inductively coupling, via an inductive link, a sensor deployed in the user with an external user device; powering the sensor via the inductive link; and performing initial pairing of the sensor and the user device with the inductive link. The initial pairing can comprise exchanging security information. The inductive coupling can comprises generating a quasi-static H field.

Other aspects, advantages, and salient features of the invention will become apparent to those skilled in the art from the following detailed description, which, taken in conjunction with the annexed drawings, discloses exemplary embodiments of the invention.

BRIEF DESCRIPTION OF THE DRAWINGS

The invention will be more readily understood with reference to the illustrative embodiments thereof illustrated in the attached drawing figures, in which:

FIG. 1 depicts operations of existing physiological condition monitors;

FIG. 2 depicts operations of a physiological condition monitor in accordance with an illustrative embodiment of the present invention;

FIGS. 3, 4A, 4B and 5 each depict a continuous physiological condition monitoring system in accordance with illustrative embodiments of the present invention;

FIGS. 20A, 20B and 20C depict a continuous physiological condition sensor in accordance with an illustrative embodiment of the present invention.

Throughout the drawing figures, like reference numbers will be understood to refer to like elements, features and structures.

DETAILED DESCRIPTION OF ILLUSTRATIVE EMBODIMENTS

Overview

Figure 3:
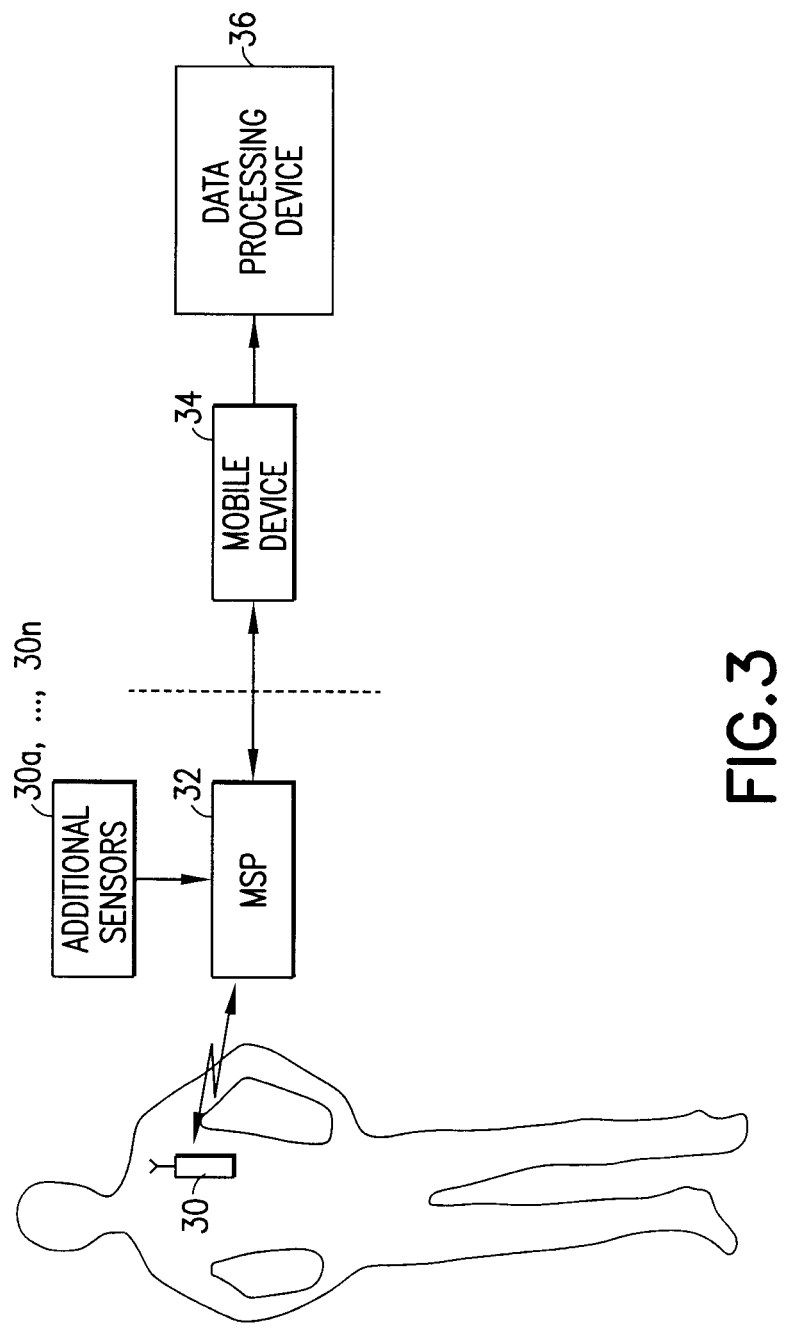

In accordance with illustrative embodiments of the present invention and with reference to FIG. 2, a physiological condition monitoring device provides a user with information derived from measured data (block 20) that is easy for the user to understand and use. For example, the physiological condition monitoring device can present the information to the user in a video mode wherein a video image of a person or other entity explains selected and interpreted measured data to the user. For example, with reference to block 24 of FIG. 2, the physiological data and other optional information can be interpreted and then information that a user needs to know can be determined based on the interpreted data (e.g., selected data points and/or data patterns, or retrospectively or prospectively determined data points) and, for example, a prescribed medical treatment protocol or, optionally, recommended user actions to prevent or lessen the impact of the selected data points or both (e.g., using a rules engine). The information that is selected for output following automated interpretation of measured data can be text, audio, video, graphical, multimedia, and so on.

In accordance with an illustrative embodiment of the present invention, the measured physiological data can be sent or inputted automatically to a cache file (block 22) for analysis and interpretation (e.g., with other data), and is then used to populate open fields and other data structures or elements that are configured with user data and defined within an output segment management system. The output segment management system comprises predetermined segments of video, as well as other types of predetermined output segments such as text segments and optionally audio segments that could also be extracted from the video segments or synthesized to speech from the text segments (e.g., text-to-speech conversion) or other representation of output segments (e.g., binary or hexadecimal codes). The output segment management system automatically constructs the information that is to be output to the user (block 26) using selected predetermined output segments which can be edited as needed to include selected measured data or pattern information automatically interpreted from the measured data (e.g., recurring patterns or other historical or prospective data indicating a problem that should be addressed or a data point exceeding a threshold and setting off alarm such as pattern of alarm events), among other user data such as recent events (e.g., meal-times, forthcoming events, stress events, exercise events, and the like). For example, the selected output segments can be streamed, concatenated, overlaid, spliced together, outputted on respective portions of a display, or otherwise combined. Further, the selected output segments can be streamed, concatenated, overlaid, spliced together, outputted on respective portions of a display, or otherwise combined with inserted or otherwise incorporated user data as needed, to create information that is meaningful, easy to comprehend, and user configurable in terms of format and delivery method(s). The selection of output segments is also described below with reference to FIGS. 5-9.

In accordance with illustrative embodiments of the present invention, the improved methods, devices and systems for providing improved (e.g., more meaningful and/or more easily comprehended) information about monitored physiological data can be used to manage a number of different physiological conditions using measurements of a number of different physiological data. A diabetes management system is described for illustrative purposes, but it is to be understood that the improved methods, devices and systems can be used for management of other physiological conditions such as, but not limited to, arrhythmia, heart failure, coronary heart disease, diabetes, sleep apnea, seizures, asthma, chronic obstructive pulmonary disease (COPD), pregnancy complications, tissue or wound state, state of wellness and fitness of a person (e.g., weight loss, obesity, heart rate, cardiac performance, dehydration rate, blood glucose, physical activity or caloric intake), or combinations thereof.

Examples of Physiological Data

Some examples of measured or monitored physiological data include, but are not limited to ECG, EEG, EMG, SpO2, tissue impedance, heart rate, accelerometer, blood glucose, coagulation (e.g., PT-INR or prothrombin time (PT) and its derived measures of prothrombin ratio (PR) and international normalized ratio), respiration rate and airflow volume, body tissue state, bone state, pressure, physical movement, body fluid density, skin or body impedance, body temperature, patient physical location, or audible body sounds, among others, or a combination thereof.

The measured data can also be related to analytes such as, but not limited to, a substance or chemical constituent in a biological fluid (for example, blood, interstitial fluid, cerebral spinal fluid, lymph fluid or urine) that can be analyzed. Analytes can include naturally occurring substances, artificial substances, medicaments, metabolites, and/or reaction products. By way of examples, on or more analytes for measurement can be glucose; insulin; acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-.beta. hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free .beta.-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, .beta.); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

Salts, sugar, protein, fat, vitamins and hormones naturally occurring in blood or interstitial fluids can also constitute analytes, for example. Further, the analyte can be naturally present in the biological fluid, for example, a metabolic product, a hormone, an antigen, an antibody, and the like. Alternatively, the analyte can be introduced into the body such as, for example but not limited to, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions can also be considered analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

Examples of Users

The methods, devices and systems described in accordance with illustrative embodiments of the present invention can provide improved information regarding a measured physiological data to different types of users having varying skill levels (e.g., medical, technical) and involvement with the patient. For example, the user can be the patient, the patient's family member or other non-medical caregiver, medically trained healthcare personnel in various ambulatory and non-ambulatory healthcare settings, school nurses or administrators, and so on.

The formatting of the improved information can be configured to accommodate different types of users. For example, different formats can be, but are not limited to:

Simple, personalized information for the patient/user in plain English or other language (e.g., minimal medical or technical terms);

Interactive information with virtual coach (e.g., a computer-generated representation of a coach or other person, animal, character), including reminders, retrospective and prospective analysis options, meaningful graphs for patient user, or non-medically trained caregiver, or healthcare providers in ambulatory or non-ambulatory healthcare settings; or Tutoring information for non-medically trained caregiver (e.g., new patient or a family member), or other care giver with or without medical training such as, but not limited to, school nurses attending multiple students.

Physiological Data Measuring Device

FIGS. 3 and 4 depict an illustrative physiological condition sensor or other device 30 for measuring and/or monitoring physiological data of a patient. Examples of sensors or measuring devices can be, but are not limited to, continuous glucose monitors (CGMs); monitors for pulmonary and/or cardiac functions such as arrhythmia, heart failure, coronary heart disease, asthma, COPD, and sleep apnea, among others; monitors for body temperature, diabetes, seizures, pregnancy complications, wound state, and so on; or combinations thereof. In some illustrative embodiments, the systems and methods are used to manage a condition related to the state of wellness and fitness of a person such as, but not limited to, weight loss, obesity, heart rate, cardiac performance, dehydration rate, blood glucose, physical activity or caloric intake, or combinations thereof.

The sensor 30 can be deployed, for example, as an internal patch, subcutaneous sensor, internal or external electrode, intravenous sensor, or any other sensor or monitoring device with telemetered output. The telemetered sensor or monitor 30 transmits a patient's measured physiological data via a first communication path to a medical signal processor (MSP) 32, for example. The communication path can be a wireline or wireless link. Further, a patient can have multiple sensors $30_a, \ldots, 30_n$ transmitting measured or monitored physiological data to a single MSP 32, as shown in FIG. 3 for example. The sensor 30 and the MSP 32, however, can be separate devices as illustrated in FIG. 3, or integrated devices as illustrated in FIGS. 4A and 4B.

With reference to FIGS. 3, 4A, 4B and 5, the MSP 32 aggregates or otherwise processes signals (e.g., measured data, or communication signals such as commands, responses, acknowledgements, status reporting, and so on) from one or more physiological condition sensors 30 and transmits the sensor signals or related data from the sensors 30 to a server or other data processing terminal 36 via a wireless or wireline data link. In FIGS. 4A and 4B, the MSP 32 (not shown) is illustrated as integrated, for example, in a user device 40, but can be separate and coupled. Further, the user device 40 can have an integrated mobile phone or cellular transceiver 34 as shown in FIG. 4A, or a separate but coupled mobile phone, or no mobile phone as shown in FIG. 4B. For example, a user device 40 can have a different type of radio frequency (RF) transceiver for local connectivity or networked connectivity to the data processing device 36. The MSP 32 can be, but is not limited to, a personal computer, a portable computer such as a laptop or a handheld device (e.g., personal digital assistant (PDA), iPod), mobile telephone such as a cellular telephone, Blackberry device, Palm device, or Apple iPhone device, a watch, a portable exercise device or other physiological data monitor (e.g., a meter connectable to a patient via a strap or incorporated into an article of clothing), a user interface connected to a vehicle bus interface, among other user devices, each of which may be configured for data communication with the sensor 30 (e.g., via a separate or integrated receiver via a wired or a wireless connection).

By way of an example, the sensor 30 can communicate with an MSP 32 via a unidirectional or bidirectional wireless communication link implementing a protocol such as, but not limited to, an RF communication protocol, an infrared communication protocol, a Wi-Fi or similar communication protocol, a ZigBee or similar communication protocol, a Bluetooth or similar communication protocol, an 802.11x wireless communication protocol, a 802.15.4 communication protocol, or other wireless communication protocol. The communication protocol can allow secure, wireless communication of several units (for example, per HIPPA requirements) while avoiding potential data collision and interference. In another illustrative embodiment, the communication link between the sensor 30 and MSP 32 can be a wired connection including USB connection, mini USB connection, or any other suitable wired or cabled connection.

In accordance with another aspect of the present invention, the MSP 32 and/or user device 40 (e.g., with integrated DSP 32) is connected to a data processing device 36 for storing, retrieving and updating data and other information corresponding to the monitored physiological condition of the patient. The data processing device 36 can be, for example, a server, or a database or other storage device(s) and associated processing device(s) for accessing, storing and processing data and information on the storage device(s). In accordance with illustrative embodiments of the present invention, the data processing device 36 can be provided with one or more of a rules engine, program code, field-programmable gate area (FPGA), application-specific integrated circuit (ASIC) or other means for controlling the processing of the monitored physiological data and related information of the user.

With reference to FIGS. 3, 4A, 4B and 5, the data processing device 36 can be local, or remotely located, with respect to the sensor 30 and the MSP 32 and/or user device 40. Separating storage and processing-intensive operations from an MSP 32 and providing them to a data processing device 36 in this manner allows the MSP 32 functionalities to be integrated into existing consumer products, for example. Accordingly, the user or the patient can enable or use the monitoring system (e.g., the sensor(s) 30 and MSP 32), while minimizing the number of additional devices to carry around or wear in the user's clothing, or on a belt with a belt clip, for example. It is to be understood, however, that the sensor 30, MSP 32 and data processing device 36 can be integrated into a single device, or can otherwise be paired in different configurations, in accordance with alternative illustrative embodiments of the present invention. The sensor 30, MSP 32 and/or user device 40 and data processing device 36 can be configured such that each of these components performs one or more communications operations such as, but not limited to, transmit one or more signals to another one or more of these components to request information therefrom, transmit signals acknowledging receipt of information in response to such requests, maintain signal communication over predetermined time periods, periodically "ping" each other to confirm or verify the communication connection, pass encryption/decryption keys and/or device or component identification codes or unique identifier information to maintain secure data exchange between the components, among other operations for example.

As stated above and with further reference to FIGS. 4A and 4B, the MSP 32 (not shown) can be integrated into a user device 40 comprising a single housing with shared user input/output modules or units. Further, as shown in FIG. 4A, a mobile phone 34 can be integrated into the user device 40. Accordingly, the user is conveniently provided with fewer devices in the overall physiological condition monitoring system described in accordance with illustrative embodiments of the present invention to handle and carry or wear. The example user devices 40 illustrated in FIGS. 4A and 4B can be configured with or without the physiological condition sensor(s) 30, depending on how the sensor(s) 30 are deployed with respect to the user and the MSP 32. The MSP 32 can be configured to directly communicate with the sensor(s) 30 to receive and/or transmit data, signal and/or instructions or requests for information, and to communicate directly with the data processing device 36 as illustrated in FIGS. 4A and 4B. If the data processing device 36 is remote with respect to the user device 40 as shown in FIG. 4A, the user device 40 can communicate with the data processing device 36 via a cellular connection (e.g., via a mobile phone or cellular transceiver 34) or via a wireless or wired network connection. For example, the MSP 32 can communicate with a remote data processing device 36 (e.g., a server) or other system component via the Internet via one or more networks including, but not limited to, PSTN, WANs, LANs, WLAN, WPAN, ad hoc wireless networks, and so on. On the other hand, if the data processing device 36 is local with respect to the user device 40 as shown in FIG. 4B, the user device 40 can communicate with the data processing device 36 using a different transceiver (not shown) than a cellular transceiver that implements a different communication link using, for example, a wireless protocol (e.g., Wi-Fi or Bluetooth connection) or a wired connection.

Continuous Glucose Monitors (CGMs) illustrate a measuring device 30 and MSP 32 and/or user device 40. Examples of a CGM or continuous blood glucose monitoring system are, but not limited to, the FreeStyle Navigator® continuous blood glucose monitoring system available from Abbott Laboratories, the MiniMed Paradigm® available from Medtronic, and the SEVEN® PLUS System and GlucoClear® System available from DexCom, Inc.

Figure 20A:
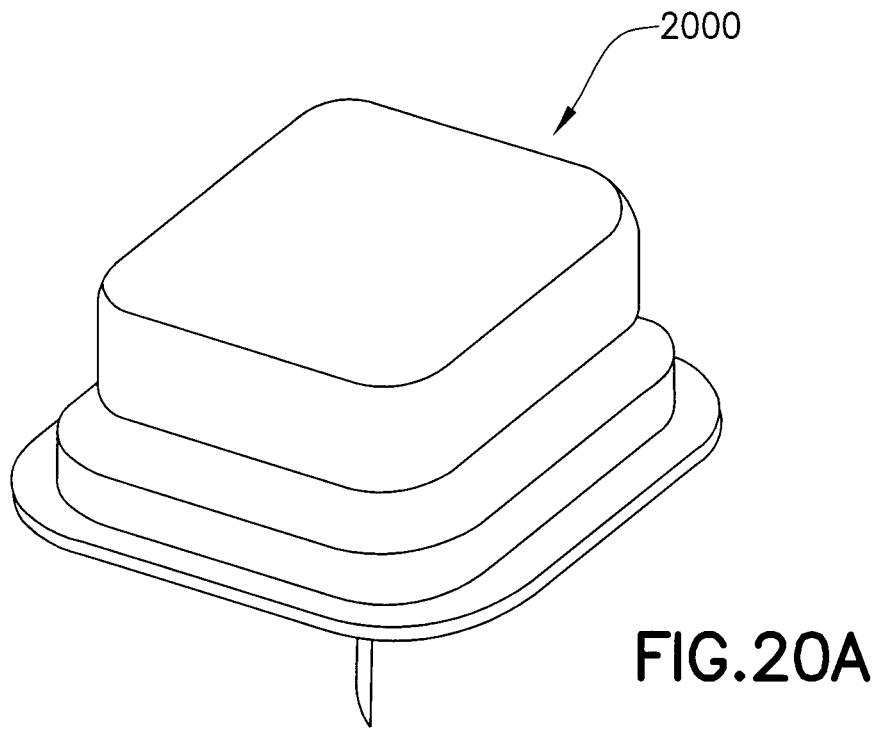
Figure 20B:
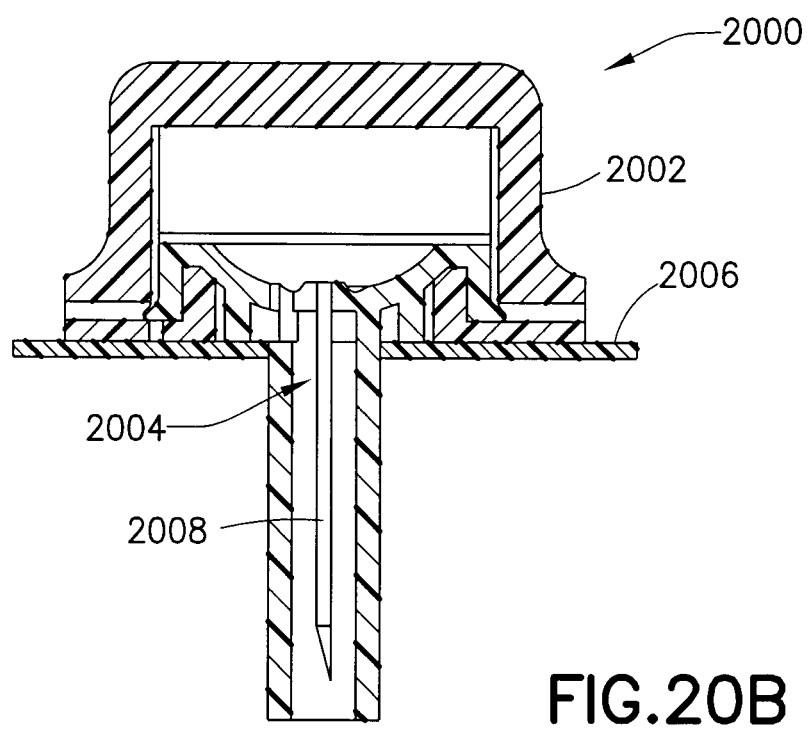

The systems and apparatuses disclosed in accordance with illustrative embodiments of the present invention, however, can be compatible with data generated by other CGMs and continuous blood glucose monitoring systems. For example, a continuous glucose monitor can have a transcutaneous or implanted sensor 30. With reference to FIGS. 20A, 20B and 20C, a continuous blood glucose sensor 2020 is depicted in accordance an illustrative embodiment of the present invention. FIGS. 20A and 20B are perspective and cross-sectional views of an illustrative transcutaneous sensor assembly comprising a housing 2002, exposed cannula 2004, and adhesive with release liner 2006 for adhering the sensor to an area on a patient's skin such that the needle 2008 penetrates the skin and provides an input from which the sensor can collect physiological data.

As shown in the exploded view of FIG. 20C, the sensor 2000 comprises a cannula subassembly 2010 and a circuit board subassembly 2012. The cannula subassembly 2010 comprises the cannula or needle 2008 mounted on a base 2014 and a coupling surface 2016 for being secured (e.g. via epoxy) to the circuit board subassembly. The printed circuit board assembly 2012 comprises a printed circuit board (PCBA) 2018 having a capacitor 2020 and a processing device (e.g., programmable processor or application specific integrated circuit (ASIC)) 2022 configured to collect samples from the cannula subassembly 2004 and convert them to measured data signals. The printed circuit board 2018 can also be provided with a wireless transmitter (not shown) to transmit the measured signals or other information to another device such as a local monitor (e.g., medical signal processor (MSP) 32 shown in FIG. 3).

It is to be understood that the sensor 30 can be a patch or otherwise implanted. For example, the sensor 30 can be configured to sense a glucose binding protein via fluorescence via a small, inserted ASIC that is, in turn, configured to wirelessly transmit the collected physiological data or representative signals. The processing device (e.g., programmable processor or application specific integrated circuit (ASIC)) 2022 in the sensor 30 is provided with program code for implementing system intelligence (e.g., as exemplified in FIGS. 5-9) such as, for example, operations described herein in accordance with illustrative embodiments of the present invention. For example, the system intelligence can provide trend analysis, predictive control, and virtual coaching and therefore more complex management behaviors than mere dosage determination. In accordance with alternative illustrative embodiments, the sensor depicted in FIGS. 20A, 20B and 20C can cooperate with an MSP 32 and optional mobile device 34, and at least some of the system intelligence can be provided in the MSP 32 (and/or optional mobile device 34) or data processing device 36.

In accordance with another illustrative embodiment of the present invention, an inductive coupling link is provided to extend product shelf-life and improve patient data security of RF-controlled devices having factory-installed, non-accessible primary-cell batteries such as an internal sensor (e.g., an internal patch, subcutaneous sensor, or internal electrode, among other sensing devices). RF receiver circuitry for the heavily used bands available to such devices demodulates and examines received signals in order to determine whether the signal is of interest to the device. This can require too much power to be performed continuously. Therefore, low-power RF devices generally synchronize with their counterparts, and thereafter operate intermittently (e.g., on a predetermined schedule).

In the case of a sealed consumable product (e.g., an implanted sensor 30), linked via RF communication to a reusable/durable user interface and control device (e.g., an MSP 32 or user device 40), deployment of a new device 30 involves, in part, the synchronization and "pairing" of the consumable device 30 and the durable device(s) 32/40. In order for this initial, unscheduled exchange to take place, the consumable device 30 must be listening for a message from an as-yet unknown instance of a durable device 32/40. Because the initial communication may occur days or months after manufacture, the consumable device's pre-synchronization listening would occur only at fairly infrequent intervals. The length of the interval would directly affect the user, as synchronization at time of deployment would require maintaining the new consumable device 30 within communication range of the durable device(s) 32/40 for at least the length of this interval prior to use.

In accordance with an aspect of an illustrative embodiment of the present invention, the inductive coupling link augments the consumable device 30 by including a second means of communication between the durable device(s) 32/40 and the consumable device 30. This second communication mechanism is used, for example, in lieu of the normal RF link (i.e., the RF link used during regular operation of the sensor 30 following initialization) for the purpose of initial synchronization and pairing. By employing inductive (e.g., a quasi-static H-field) coupling with relatively simple modulation, for example, a passive detector on the consumable product 30 can draw its operating power from the signal itself, and remain ready-to-detect at all times without consuming battery power. This improves responsiveness of the sensor 30, while extending its shelf life.

The pairing operation mentioned above allows the durable device(s) 32/40 and consumable devices 30 to exchange cryptographic keys and identifying information that ensures that subsequent communication between the devices 32/40 and 30 is secure. The pairing operation itself, however, is vulnerable to attack. If the pairing is compromised, the security of subsequent operations may also be compromised. By using an inductive coupling link to perform certain steps of the pairing operation, however, the security of the transaction is greatly increased because of the unlikelihood of the short-range, relatively nonstandard inductive coupling transmission being correctly received and decoded.

System Components

Figure 5:
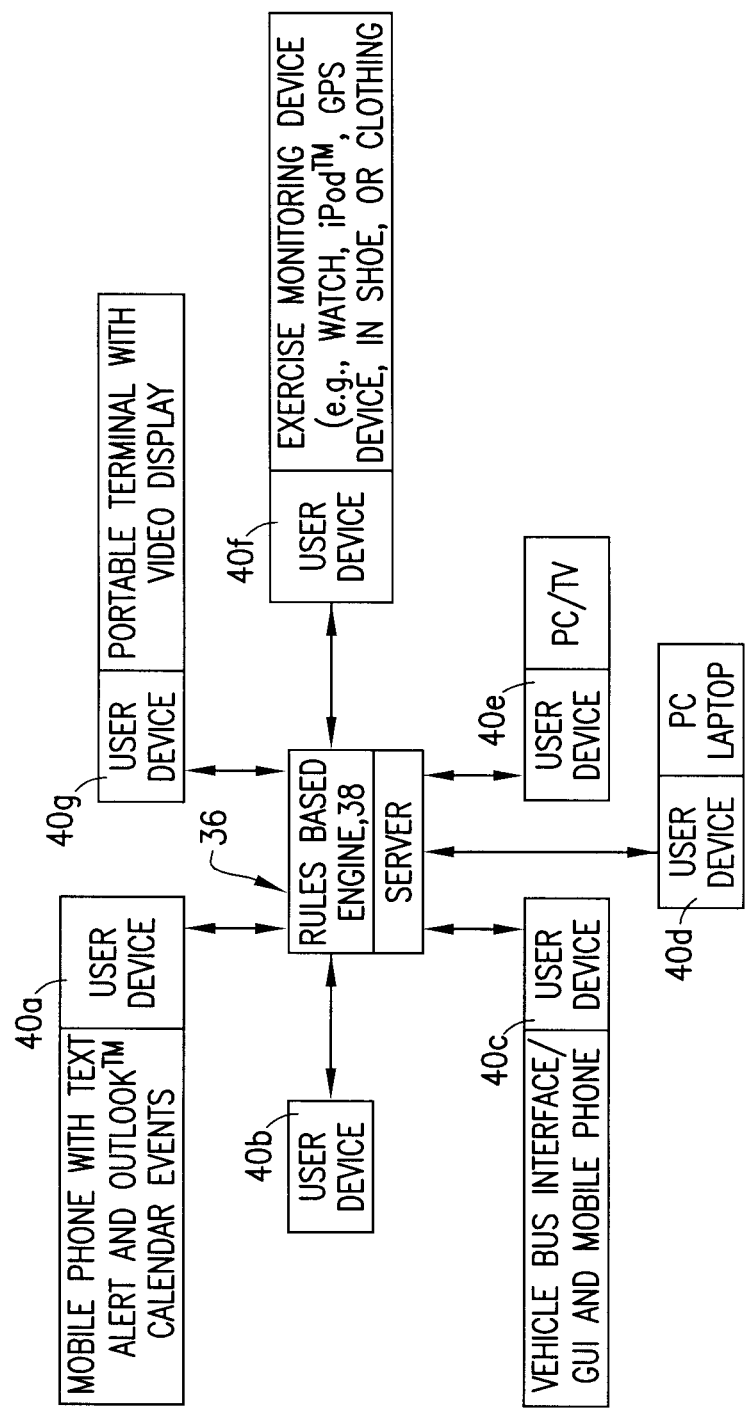

As shown in FIG. 5, a plurality of different illustrative patients' or users' devices 40 having or coupled with sensor(s) 30 (not shown) and corresponding MSPs 32 (e.g., with or without a mobile device 34) transmit measured or monitored physiological data to the data processing device 36 which can comprise a rules engine.

The user devices 40 illustrate a plurality of different methods for presenting interpreted data or information from a data processing device 36 such as a rules engine on a server, for example. It is to be understood that the user devices 40 in FIG. 5 are for illustrative purposes only and that other types of user devices and interfaces for display, playback or otherwise annunciation of information are within the scope of the present invention. For example, a user device 40 can interface with Outlook™, or employ cell phone text messaging, or interface with a vehicle bus and information system, to obtain interpreted physiological data that is presented in a meaningful and user-friendly format, and lessen the cognitive burden on the user by automatically identifying and selecting data points or patterns of which the user should be informed to manage a physiological condition, for example, and automatically providing an explanation of the identified data and optional user actions to mitigate the effects of, or occurrence of, these identified data patterns or outliers. The user devices 40 and server 36 are compatible with various physiological data collection devices (e.g., medical condition data collection devices as well as other portable training/exercise devices), and various user communication, information and/or entertainment devices.

For example, a user device 40a cooperates with a mobile phone that can provide the selected output information to a user via text alerts and Outlook™ Calendar events. User device 40b is configured, for example, to communicate directly with the data processing device 36 for reporting measured data and receiving selected output information. Illustrative user devices 40d, 40f and 40g cooperate with various portable devices for obtaining and reporting measured data to the data processing device 36, and receiving and outputting selected information from the data processing device 36. The various portable devices are, for example, a laptop or other portable terminal with video display and a portable monitoring device (e.g., for monitoring physiological conditions during exercise) such as a watch, iPod™ or GPS device (e.g., that can be worn or affixed to a shoe or clothing). User device 40c is connected, for example, to a vehicle bus interface and user interface and can communicate with the data processing device 36 via a mobile phone connection or vehicle ad hoc network (VANET) connection (e.g., using one or more of WiFi IEEE 802.11p, WAVE IEEE 1609, WiMAX IEEE 802.16, Bluetooth, Integrated Resource Analyses (IRA), ZigBee or other protocol). Such connections optimally are secured connections for data privacy and integrity. Illustrative user device 40e cooperates with a stationary device such as a personal computer (PC) or television (TV).

As stated above and with continued reference to FIG. 5, the sensor or user data collection devices 30 are connected to a data processing device 36 (e.g., server and/or programmed module implementing a rules engine) in accordance with an illustrative embodiment of the present invention. The data processing device 36 is illustrated, for example, as a server with rules-based engine for storing and processing user data such as measured physiological data from a user device 40 and determining information to be output by the user device based on the received data. As described below in accordance with an illustrative embodiment of the present invention, the outputted information can be based on a clinical protocol for managing a particular physiological condition, whereby selected data points or patterns in the physiological data provided by a user device 40 are identified, and information is selected (e.g., selected ones of predetermined output segments) for output to explain the selected points or pattern such as any optional recommended user actions, or observations of conditions that may have contributed to the identified selected data points or patterns based on the protocol(s) in the rules engine. For example, a rules engine 38 or other program code structure or module(s) can be implemented at a server or other processing device which is based on a system known as Staged Diabetes Management (SDM) that has been developed to assist medical practitioners in managing a patient's disease by comparing patient data with a set of guidelines for treatment options. SDM is described in further detail in Mazze et al., Staged Diabetes Management, A systematic Approach; International Diabetes Center; Minneapolis, Minn., 2000, which is incorporated by reference herein in its entirety. Other examples of medical health condition management protocols are discussed the article by Wilson, Mark et al., "Intensive Insulin Therapy in Critical Care, A Review of 12 Protocols," *Diabetes Care*, Vol. 30, No. 4, April 2007, pp. 1005-1011, which is incorporated by reference herein in its entirety. The rules based engine can be at least partially commercially available based on existing protocols for physiological condition management, but can be modified, for example, to automatically process additional user information inputs that are relevant to managing the physiological condition (e.g., food intake, exercise parameters such as measured heart rate, duration of physical activity, detected environmental conditions that can affect physiological conditions, and so on).

Additional interfaces and modalities for presentation of information in accordance with illustrative embodiments of the present invention are depicted in FIGS. 11-19.

Figure 6:
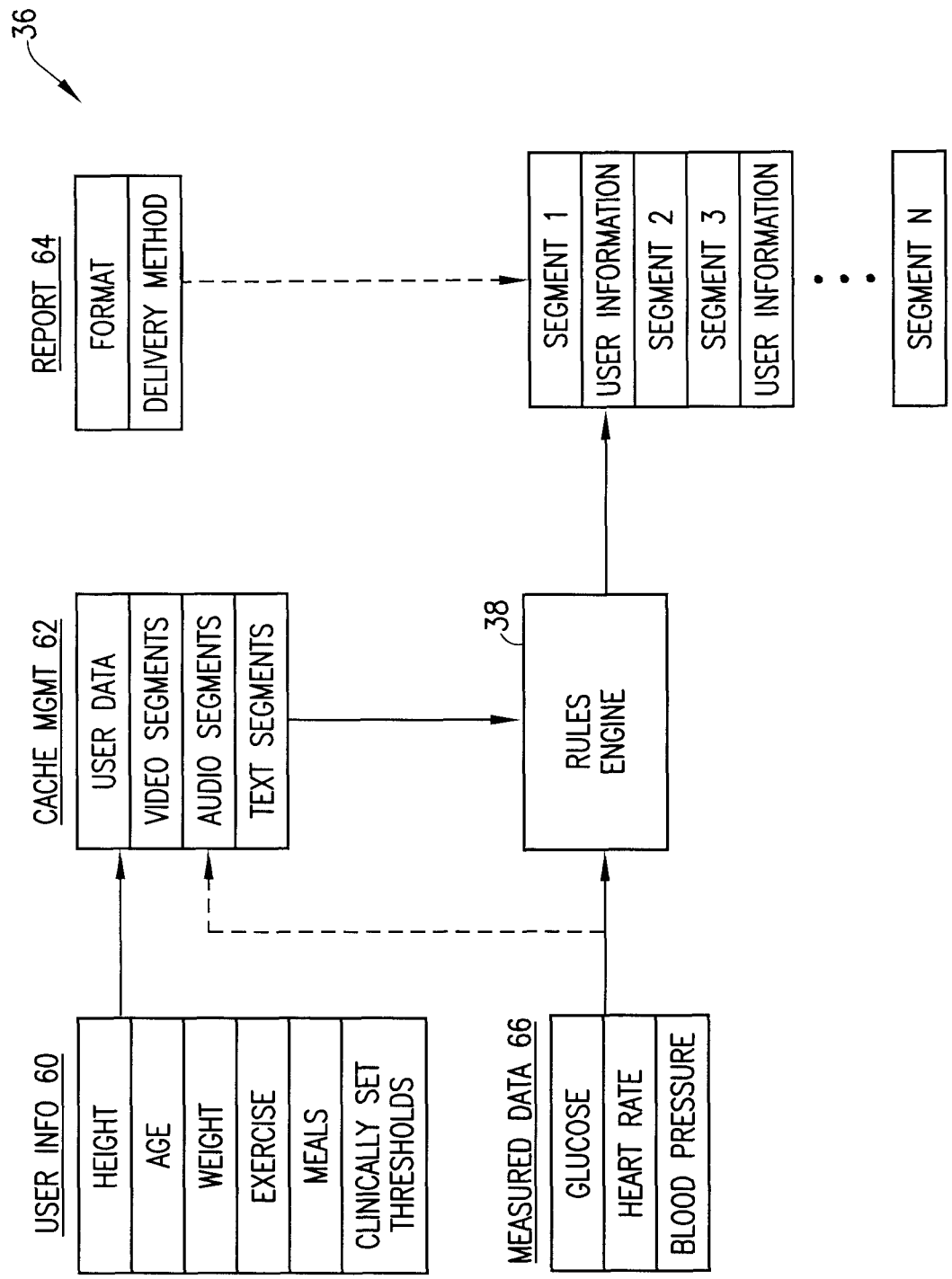
FIG. 6 is a block diagram of a cache management system for presentation of interpreted physiological data in accordance with an illustrative embodiment of the present invention.

FIG. 6 depicts illustrative components for selecting interpreted data output in accordance with an illustrative embodiment of the present invention. A cache management system or other type of data management system 62 receives and stores, for each user, user configuration data 60 and optionally measured inputs 66. The measured inputs can also be provided directly to the rules engine 38. The user configuration data 60 can be, but is not limited to:

Age
Weight
Carbohydrates ingested and Meal times
Exercise/activity level
Monitoring device type(s)
Insulin or other medication or substance delivery profile
Environmental conditions impacting user
Blood glucose meter (BGM) readings or other physiological data (e.g., other analytes or patient vitals information such as heart rate, or body temperature)
Thresholds: e.g., hypoglycemic, hyperglycemic, outside hypoglycemic and hyperglycemic thresholds, within both thresholds; selected per user (e.g., by physician)
Preferred output formats (e.g., audio, text, video or other audiovisual (A/V), graphical, multimedia, and so on)
Preferred output devices (TV, PC, vehicle user interface, PDA, mobile phone, mobile device, medical instrument or device)

The cache management system 62 also stores video segments, audio segments, and/or text segments, that is, stores and uses information segments (e.g., snippets, phrases, or other parts of the outputted information) that provide information based on selected data including, but not limited to, selected data points or summary of selected data points based on retrospective analysis or prospective analysis. The output segments can be audio, video, graphical, multimedia, and/or text that can be converted to audio only and/or digital data. The output segments can also be "keys" or other index data for accessing corresponding stored video, audio only, or text output.

The rules engine 38 analyzes cached user data and device data readings to generate selected information output such as selected segments based on thresholds and/or certain data values over a period of time (e.g., the same daily time period over multiple days) to instruct a user as to highlights of historical data, or recurring patterns, or explanation of why highlighted data likely occurred, and/or suggested user action by streaming or otherwise concatenating or combining the selected output segments together, with or without inserted user information as needed, in a format and on a device selected by the user.

Example reports or outputted information includes, but are not limited to data highlights or patterns as exemplified in FIGS. 11-19 (e.g., on wrist watch, TV, PC, laptop, mobile phone, PDA, vehicle bus and GUI, among others using text, graphs, video, audio, Outlook™ or other calendar reminders, text messaging, and so on).

Illustrative Processing of Measured Physiological Data and Output Selection

FIGS. 7-10 depict illustrative flow charts for processing measured physiological data and other inputted information to select an output (e.g., predetermined audio, visual, multimedia, graphical outputs with or without selected measured data or other user information) to provide selected information to a user (e.g., interpreted physiological data with an explanation of why and/or when it occurred and optionally instructions to manage the associated physiological condition in view of the interpreted physiological data) in accordance with illustrative embodiments of the present invention. The operations exemplified by FIGS. 7-10 can be implemented, for example, via the data processing device 36, which can be a server or other processing device operating with an integrated rules engine or in conjunction with a separately coupled rules engine and is programmed (e.g., via software instructions) or otherwise configured to perform the operations.

The operations exemplified by FIGS. 7-10 are described in the context of blood glucose monitoring for illustrative purposes. That is, the measured physiological data are analyte measurements such as the amount of glucose in a patient's blood. It is to be understood, however, that the operations of the data processing device 36 and user device 30 described in connection with FIGS. 7-19 are applicable to other physiological data and monitored physiological conditions that are exemplified, but not limited to, the afore-mentioned examples of physiological data, and physiological conditions for which these physiological data may be deemed as indicators. In addition to inputted measured physiological data, other selected inputted information can be, but is not limited to, meal times, food intake, prescribed testing times, medication delivery times and amounts, exercise, and conditions that may impact the physiological condition such as exercise and environmental conditions (e.g., detected travel in traffic congestion or other stressors), as illustrated in connection with FIGS. 11-19. Further, the examples provided in FIGS. 11-19 provide the user with instructions for how to mitigate the interpreted physiological data to manage the associated physiological condition, but it is to be understood that the selected outputs can provide instructions for encouraging the user to repeat or otherwise sustain the interpreted physiological data such as when the interpreted physiological data is selected by the rules engine to illustrate to the user that the patient is complying effectively with the protocol prescribed to manage his or her associated physiological condition.

Figure 7:
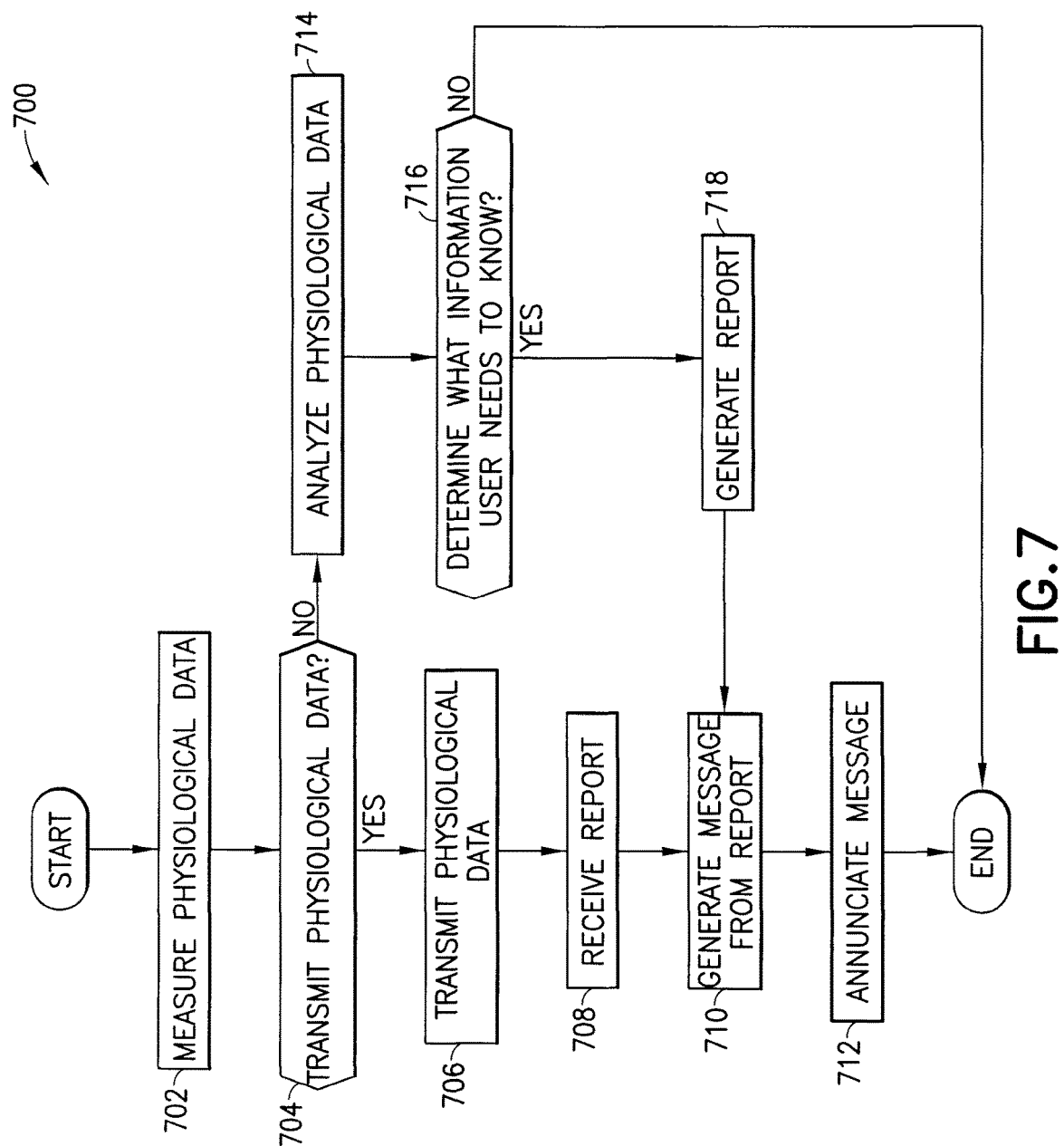
FIGS. 7-10 are flow charts depicting processing of physiological data and generation of presentations of physiological condition management information in accordance with illustrative embodiments of the present invention.

With reference to FIG. 7, a user device 40 can be programmed (e.g., software instructions provided to a processing device (e.g., MSP 32) in the user device 40 or associated with the user device) or otherwise configured to measure or detect specified physiological data, or receive measured physiological data from one or more sensors 30, as indicated at 702. For example, an illustrative user device 40 (e.g., a CGM) transmits blood glucose readings and optionally other data or information (e.g., one or more of user information and output preferences such as the items of information mentioned above in connection with user configuration data 60 in FIG. 6) to a data processing device 36 (e.g., server) for analysis as indicated at 704 and 706.

As will be described with reference to FIGS. 8 and 9, the data processing device 36 can analyze the measured physiological data and optionally other data or information such as selected items from the user configuration data 60 in connection with one or more parameters, conditions, thresholds and auxiliary data specified by a rules engine or other processing module configured to manage a designated physiological condition (e.g., in accordance with a medically accepted or otherwise prescribed protocol) to determine what information a user needs to know and, correspondingly, what selected outputs need to be generated at the user device 40 to annunciate this selected information (e.g., see blocks 804, 806, and 906, 912, 918 and/or 924). The data processing device 36 can generate a report or other type of output (e.g., see block 810) for transmission to the user device (e.g., via a wireless or wireline link), as indicated at 708. For example, the report can be a signal, a series of signals, an electronic document, one or more XML pages, program code, data stored on a computer-readable memory device for access by the user device, among other formats. The report can contain instructions for the user device 40 to annunciate selected output segments and optional selected user data based on the determination of what information a user needs to know in view of the measured physiological data and other factors (e.g., factors specified in the user configuration data 60). The instructions can contain the output segments themselves (e.g., where predetermined segments or complete messages of audio, video, multimedia and/or text are stored at, or otherwise accessed from an separate memory, by the data processing device 36) or instructions for where to access the output segments or to generate the output segments via the user device 40.

In accordance with an alternative embodiment of the present invention, the user device 40 can analyze the measured physiological data (block 714) to determine what information a user needs to know (block 716) and, correspondingly, what selected outputs need to be generated at the user device 40 to annunciate this selected information (block 718). The analysis performed by the user device 40 in block 716 can be the same as, or a subset of, the analysis performed by the data processing device 36 and exemplified with reference to blocks 804, 806, and 906, 912, 918 and/or 924. Thus, in the event that communication with the data processing device 36 is not possible, the user device 40 can remain able to determine, at some level, if the user needs to be provided with information concerning selected measured physiological data.

By contrast, analysis performed by the data processing device 36, as opposed to the user device 40, can be advantageous since this allows the algorithm for determining output information at the server or other data processing device 36 to be easily updated at a central location without having to update the sensors 30 and/or user devices 40 themselves. Further, the storage capacity of the data processing device 36 can be significantly greater than that of a user device 40 and thereby allow for more storage, for example, of output segments, user information and/or measured data (e.g., historical or past measured data that is being archived). In addition, the processing power of the data processing device 36 can be significantly greater than that of the user devices 40 and thereby allow for more complex analysis (e.g., based on historical data, or significant amounts of data, or data from other sources) that may not be available to the MSP 32 or the user device 40.

With reference to block 712 in FIG. 7, the user device 40 is programmed to generate a message for the user in accordance with the report or other instructions for generating outputs received from the data processing device 36 or outputs generated by the user device 40. The user device 40 is either preconfigured, or receives instructions (e.g., in a report), as to which type of device is performing the annunciation of the message (e.g., speaker and/or display screen of a TV, PDA, mobile phone, vehicle interface, etc.) and the format of the message (e.g., text, web page, graphical presentation, audio, audiovisual, multimedia, video, and so on). As stated above, the report can contain message segments selected and provided by the data processing device 36, or message identifiers and instructions on where to access them in storage (e.g., via a WiFi connection if the user device is a web-enabled device), or instructions for synthesizing or otherwise producing the message. The report can also provide instructions to the user device 40 for how to incorporate certain data into a message (e.g., selected measured physiological data points, dates, times or other auxiliary data to explain the occurrence of selected data points or a pattern). These instructions for incorporating data into a message can also be configured or otherwise programmed in the user device 40 (e.g., in program code stored at the user device, or code instructions stored with the output segments, or encoding in an output segment, and so on) as opposed to providing them in a report.

In addition, either the measured physiological data or the user configuration data 60 provided to the data processing device 36, or data available at the user device 40, can indicate the intended recipient of the message to facilitate selection of output segments for an appropriate message for that recipient. For example, when measured physiological data is outside a prescribed range and corrective action must be taken, a message on a user device 40 being operated by a trained medical professional on behalf of a patient may be different from a message for the patient. For example, a message can be generated based on the same interpreted information (e.g., outlier physiological data over a designated time period); however, the output segments selected for that message in the context of a nurse operator of the message-generating user device 40 may contain more technical or medical terms and other care procedures (e.g., a medical staff message that states "a hyperglycemic event is predicted at x time during the y time period of the day for patient z. A modification to patient z's care protocol may be needed.") than the output segments selected for that message in the context of a patient operating the message-generating user device 40 (e.g., a patient message that states "Your blood sugar appears to be getting higher at x time during the y time period of the day. Please review your plan of care with your doctor.")

Figure 8:
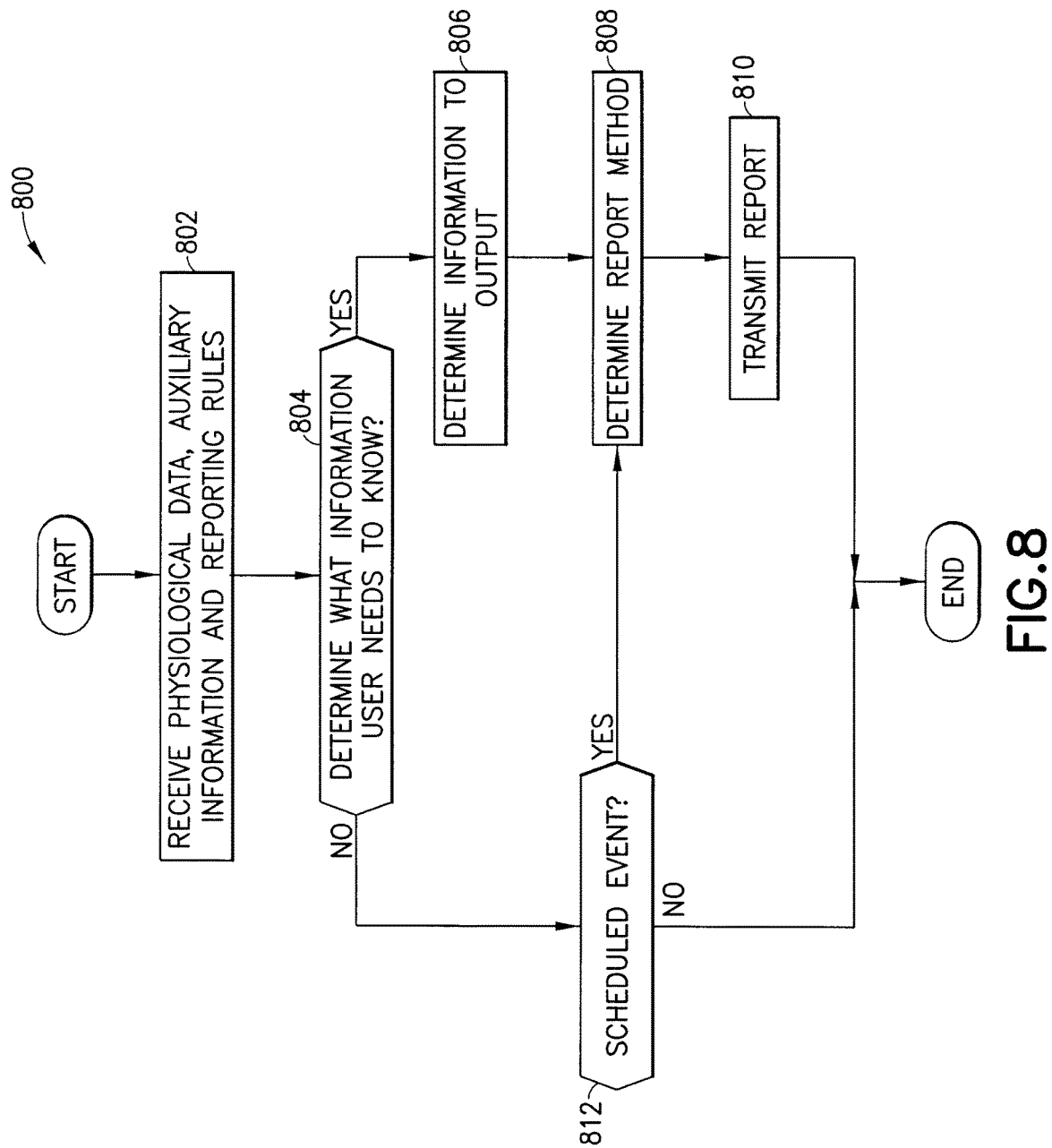

FIG. 8 illustrates example operations indicated generally at 800 that can be performed by the data processing device 36 in accordance with an illustrative embodiment of the present invention. As mentioned above, one or more processors associated with the data processing device 36 can be programmed or otherwise configured to perform these operations. With reference to block 802 in FIG. 8, the data processing device 36 receives physiological data from the user device 40 and/or the sensor(s) 30. The data processing device 36 can also receive auxiliary data (e.g., user configuration data 60), and optionally reporting rules (e.g., user preferences for receiving outputted messages or other information related to the interpreted measured physiological data, type of user, message format and output device, for example, provided as part of the user configuration data 60 or separately provided). Physiological data is measured data of the user (e.g., glucose, heart rate, blood pressure, etc.) provided by one or more sensors 30. Auxiliary data can be, but is not limited to, historical data (e.g., previous analyte measurements or measured physiological data, past medication administration), user data (e.g., weight, age, carbohydrates, exercise, prescribed treatment regimen parameters, etc.), and any other data that is used (e.g., by the rules engine 38) to determine when the user needs to be presented with information regarding interpreted measured physiological data and management of a related physiological condition. Reporting rules are based on the types of information that can be selected and provided to a user, as well as user configuration data 60 identifying, for example, the type of user, and how to report an event to a user such as user device type and format of the message being annunciated (e.g., text message to the user's cell during a meeting, an alarm on the monitor, etc.).

Using information such as the measured physiological data and optional other information described in connection with block 802, the data processing device 36 determines what information to provide to the user, as indicated at blocks 804 and 806. An example of how the data processing device 36 determines what information to provide to the user is described in connection with FIG. 9. An example of how the data processing device 36 determines what output segments and other information to provide in a message is described in connection with FIG. 10.

In accordance with another illustrative embodiment of the present invention, the data processing device 36 can be scheduled to provide a user device with selected interpreted information (e.g., programmed to generate a custom report pursuant to a particular patient plan of care, or to generate a message at a selected time and/or day or in response to a designated criteria, or preconfigured to provide selected data based on type of user 40, among other examples), as indicated at 812. Similarly, with reference to blocks 714 and 716 in FIG. 7, the user device 40 can be scheduled to provide selected interpreted information in an outputted message, that is, as opposed to automatically generating such an outputted message whenever the interpreted information indicates that such a message is needed. Scheduled message generation can be optional.

With reference to block 808 in FIG. 8, the data processing device 36 determines the reporting method for generating the message, and then transmits the report to the user device 40 as indicated at 810. As mentioned above, different user devices 40 can employ different media for providing a message to a user such as, but not limited to, an audio message played through a speaker coupled to the user device 40, or a graphical, text, video, or multimedia message presented via a display and/or speaker coupled to the user device 40. User configuration data 60 such as reporting rules can also provide parameters used by the program control of the data processing device 36 to determine which output segments to use to generate a particular message depending on media type, user type and device type, among other configuration parameters.

With reference to block 708 and block 810 in FIGS. 7 and 8, respectively, the user device 40 and data processing device 36 can be programmed or otherwise configured to send acknowledgement signals when, for example, data is sent from the user device 40 to the data processing device 36, or reports are sent from the data processing device 36 to the user device 40, and the data or report is successfully received. In addition, the user device 40 and data processing device 36 can be programmed or otherwise configured to retransmit data or a report, respectively, a selected number of times or during a selected time period when an acknowledgement signal is not received (e.g., within the selected time period).

Figure 9:
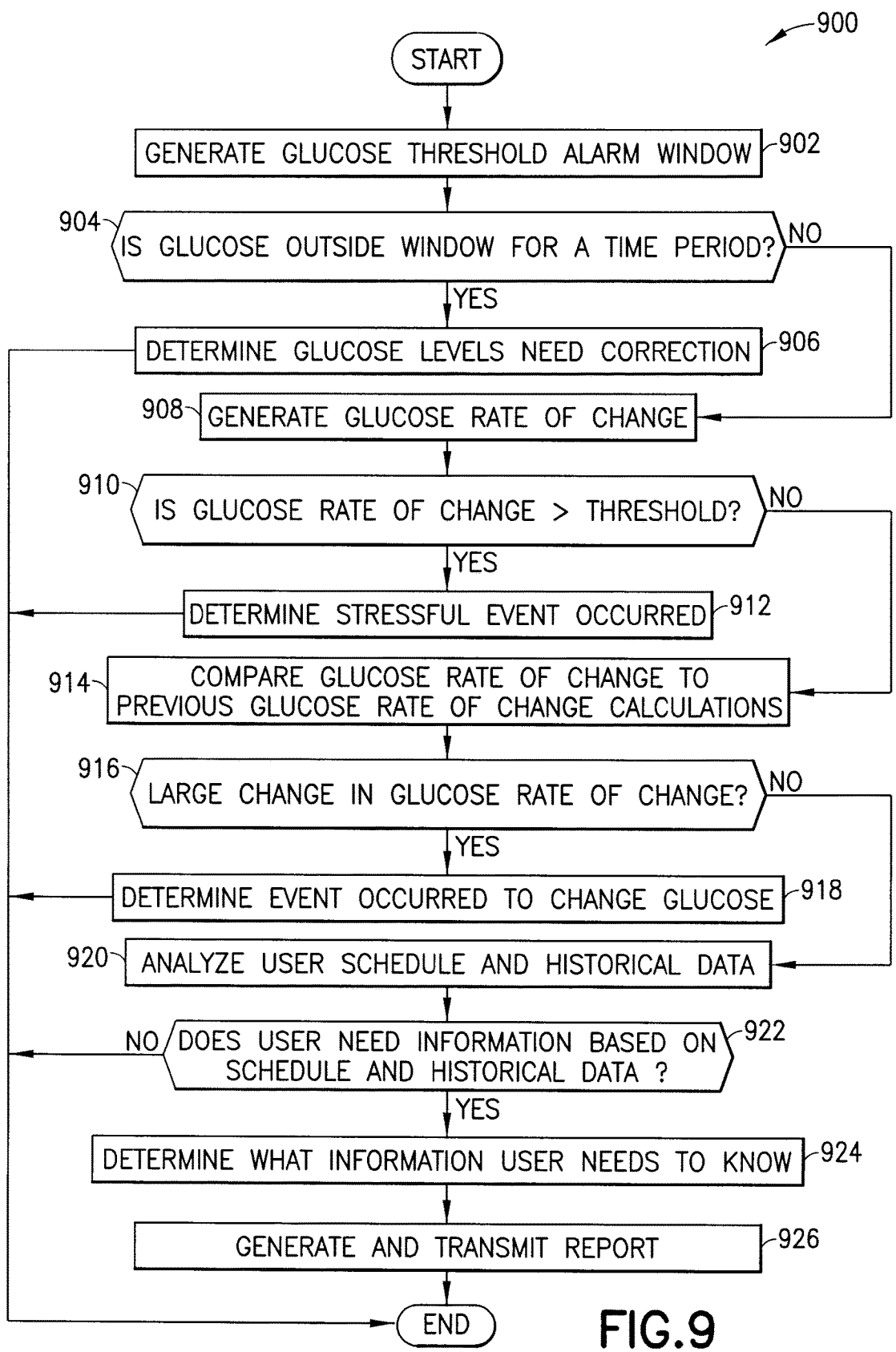

FIG. 9 illustrates operations of an example rules engine or other program code module or programmed device that can interpret physiological data and optionally other inputted information and determine what a user needs to know in accordance with illustrative embodiments of the present invention. The example rules engine or other program code module or programmed device described in connection with FIG. 9 can be deployed integrally in, or separate from but coupled to, a user device 40 (e.g., see block 716 in FIG. 7) or a data processing device 36 (e.g., block 808 in FIG. 8). It is to be understood that the example rules engine or other program code module or programmed device is configured to provide more than conventional output of one or more data points that do not meet a selected threshold or criteria, or a detected trend in the data points over a specified time period. As described below, the example rules engine or other program code module or programmed device is also configured to detect patterns in measured physiological data (e.g., measured data within a selected time period during a day over several different days or months), and to generate outputs based on user device type, desired message media type and user type that explains the occurrence of the data and optionally recommended user actions.

For example, in the context of diabetes management, illustrative interpretation of physiological data is described with reference to blocks 902, 904, 910, 916 and 920. It is to be understood that other criteria can be used by the example rules engine or other program code module or programmed device, and that the interpretation (e.g., criteria) can be in the context of managing other types of physiological conditions. Some of the parameters (e.g., thresholds, ranges of data point values, among others) can be based on medically accepted parameters for managing a physiological condition or can be custom designated parameters.

By way of an example, the example rules engine or other program code module or programmed device is configured to first generate a glucose threshold alarm window based on the user's physiological data (block 902). If the user's current glucose level is outside the alarm window (block 904), then the example rules engine or other program code module or programmed device determines the user's glucose levels need correction (block 904) and, accordingly, determine what information the user needs to know (e.g., selected data and output segments).

With reference to block 908, the example rules engine or other program code module or programmed device determines a glucose "Rate of Change." For example, a glucose "Rate of Change" can be a glucose prediction in DT minutes (e.g., about 10 minutes prospectively in units of mg/dL/min) based on current glucose value and rate of change. For example, if one's current glucose is 80 mg/dl and rising fast, that is not a problem. If, however, one's glucose is 80 mg/dl and falling fast, that is a problem because, at this current glucose level and rate of change, the patient may experience hypoglycemia in a few minutes if no action is taken. Conversely, if a patient's glucose is 230 mg/dl and falling, that is no problem. If, however, it is 230 mg/dl and rising, then the patient may experience hyperglycemia in a few minutes if no action is taken. Accordingly, if the predicted glucose is greater than a set hyperglycemic threshold (i.e., 250 mg/dl) or less than a set hypoglycemic threshold (i.e. 70 mg/dl), the user is alerted (910,912) and, correspondingly, data and output segments are selected based on this determination of what the user needs to know.

Predicted glucose can be calculated, for example, as:

$$\text{Predicted glucose} = \text{Current Glucose} + DT^*(\text{Rate of Change or velocity of Glucose})$$

where future glucose is assumed to be a linear extrapolation of current glucose (constant velocity), and DT can be 15 minutes (e.g., if glucose is being predicted 15 min in the future).

Near the hyperglycemic and hypoglycemic extremes glucose dynamics tend to curve (decelerate) as they approach peaks and nadirs. Therefore, glucose can also be extrapolated via a quadratic function such as, for example:

$$\text{Predicted glucose} = \text{Current Glucose} + DT^*(\text{Velocity of Glucose}) + \tfrac{1}{2}^* DT^{\wedge}2^*(\text{Acceleration of Glucose})$$

This formula yields less alarms; however, in order to determine a true versus false alarm, the patient would have to take no corrective action to see if the predicted glucose in 15 minutes was, in fact, correct. It is to be understood that other prediction algorithms and methods can be employed by the example rules engine or other program code module or programmed device to determine, for example, a rate of change for a designated parameter in the physiological data.

With continued reference to FIG. 9, the example rules engine or other program code module or programmed device compares the current glucose rate of change with previous glucose rate of change calculations that have been stored (914, 916) to determine if an event occurred to change the glucose level (918) such as when a large change above a specified amount is determined and there is information a user needs to know. For example, the rules engine or other program code module selects corresponding data and output segments for generating a message or presentation or report. If no event occurred to change the glucose level, the example rules engine or other program code module or programmed device analyzes the user's schedule (e.g., per a prescribed plan of care as indicated in user configuration data 60) and historical data to determine if the user needs information based on the schedule and historical data (922, 924). As mentioned above, the example rules engine or other program code module or programmed device can store past physiological data and analyze current data with historical data to determine, for example, a pattern of data points occurring at the same time period during the day and over multiple days and/or in conjunction with other user data (e.g., user information relating to exercise, food intake, medication administration, environmental or stressor/trigger data, among other information).

The determination and comparison of a rate of change of selected physiological data to designated thresholds (blocks 910 and 916) by the example rules engine or other program code module or programmed device can be useful, for example, to mitigate the impact of environmental conditions or a stressful event or other trigger in the patient before the patient is even aware that corrective measures may be needed to manage a monitored physiological condition. For example, a user can be driving and not able to immediately take corrective measures upon actual onset of symptoms of hypoglycemia. In accordance with illustrative embodiments of the present invention, the example rules engine or other program code module or programmed device can generate a message, or report to facilitate the generation of a message, in response to a determination of what information a user needs to know as exemplified in blocks 906, 912, and 918 and notify the user via the message with an explanation of the interpreted data (e.g., what has occurred, and optionally why or what corrective actions to undertake). In any event, such messages provide targeted content for physiological condition management that is user-friendly (e.g., explains what the selected physiological data points are and why they are significant to the user) and does not overwhelm the user with otherwise irrelevant information.

The example rules engine or other program code module or programmed device described with reference to FIG. 9 can be implemented in conjunction with memory at the user device 40 or data processing device 36 for storing different sets of operations for interpreting the physiological data and other information for the same physiological condition, as well as for storing different sets of operations for interpreting different physiological data and other information for other physiological conditions. The user configuration data 60 can specify which sets of operations to use to interpret the inputted information.

The memory associated with the example rules engine or other program code module or programmed device can also store other information besides data relating to the physiological condition such as environmental or stressor/trigger sensor data (e.g., ambient temperature, air quality, telematics-enabled vehicle bus data indicating a potentially stressful event such as driving in traffic congestion, and so on). The example rules engine or other program code module or programmed device can be configured to weight the input of such environmental or stressor/trigger data during the determination made in, for example, block 910 or 910, such that lower rate of change may still be deemed a prediction of a possible event and cause the generation of a report or message earlier (or at all) than if no environmental or stressor/trigger data was available.

Figure 10:
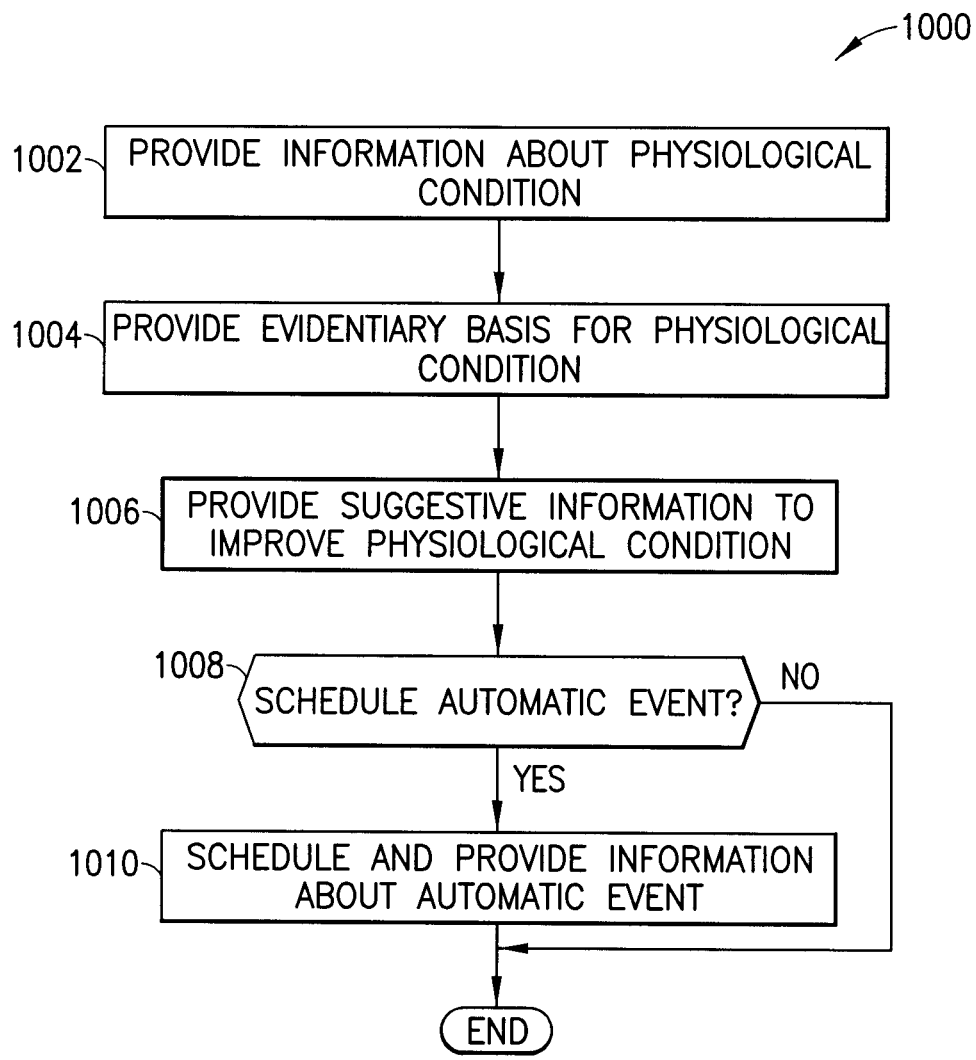

With reference to FIG. 10, once the example rules engine or other program code module or programmed device determines what information the user needs to know (e.g., blocks 716 and 806 as exemplified in FIG. 9, blocks 906, 912, 918 and 924), they select a message and one or more output segments to generate the message (i.e., or for inclusion in or at least referenced by a segment identifier in a report to facilitate generating the message) in accordance with illustrative embodiments of the present invention. For example, a memory associated with and accessible by the example rules engine or other program code module or programmed device can store output segments used to generate one or more designated messages in response to a designated range of interpreted physiological values for the determination in block 906, 912, 918 or 924. For example, a message can be stored for block 906 and corresponding multiple output segments to generate the message based on user device 40 type and/or preferred message format (e.g., designated in the user configuration data 60). Further, plural messages intended for respective different types of users (e.g., medical staff, patient, non-medical caretaker of patient) can be stored for playback when the same physiological data criteria are met and then selected based on user type (e.g., as indicated in the user configuration data 60). Similarly, messages and different output segments can be stored and accessed as needed for other processing steps (e.g., blocks 912, 918 or 924 in FIG. 9 or other illustrative operations performed by the example rules engine or other program code module or programmed device for different monitored physiological conditions and their respective protocol(s) for determining what information the user needs to know.

As indicated in block 1002 in FIG. 10, a selected message or report can identify the stored output segments needed to indicate information about the physiological condition such as a segment or plural, combined segments to indicate to the message recipient that a selected physiological data parameter is outside a selected limit or range, or indicate an undesirable or desirable condition has been detected (e.g., based on the determination of what information the user needs to know as described above in connection with block 906, 912, 918 or 924 on FIG. 9, or other process step associated with another programmed protocol in the rules engine, program code, or processing device).

For example, the stored messages can be assigned unique message identifiers and can be stored with cross-referenced indices to different detected physiological conditions or determinations of what information the user needs to know (e.g., as described above in connection with block 906, 912, 918 or 924 on FIG. 9, or other process step associated with another programmed protocol in the rules engine, program code, or processing device). In other words, the same message can be used in different circumstances that are also assigned, for example, unique event identifiers. Further, different output segments can be used for the same message. Accordingly, the memory stores cross-referenced tables or other data or code structures of output segment identifiers that can be used for the same message or event but for different users, depending on user type and preferred output format. The identifiers for the message and output segments can be provided, for example, in the content or metadata of the messages or output segments themselves (e.g., as a data flag, data field, or encoded in the message content), or can be associated with a data structure (e.g., an index, key or other indicia corresponding to the respective memory locations of the message or output segments).

As indicated in block 1004 in FIG. 10, the rules engine, program code, or processing device selects interpreted physiological data or other evidentiary data (e.g. time of day, time of event, and so on) for insertion or other type of incorporation into the selected output segments representing the information about the physiological condition. As indicated in block 1006 in FIG. 10, the rules engine, program code, or processing device can optionally provide output segments in the message that provide suggestive recommendations to the user to manage the monitored physiological condition. As mentioned above, these recommendations can be to take corrective actions to mitigate certain factors impacting the physiological condition (e.g., such as the illustrative actions described in connection with FIGS. 11-13) or to encourage existing physiological condition management compliance.

For example, the illustrative rules engine, program code, or processing device can detect an event that represents information that a user needs to know, can access user configuration data 60 or other data to determine type of user, type of user device and preferred message format, as well as select a message based on the event and select output segments that are concatenated or otherwise combined to generate the message based on the cross-referenced message, event and output segment indices. The selected output segment indices can be used to retrieve corresponding pre-configured content, or instructions to generate or otherwise synthesize the corresponding content. Alternatively, the selected output segment indices can be provided in a report with other optional information for transmission (e.g., from the data processing device 36 to a user device 40). For example, the data processing device 36 or the user device 40 can be configured, for example, to access pre-stored audio content output segments, or to synthesize speech from stored text messages or portions of a message. Further, the data processing device 36 or the user device 40 can be configured to generate a video using a concatenated video segments, or to generate a selected graphic. In these instances, the indices or the content in the segments themselves can be configured to indicate where to incorporate the evidentiary data as mentioned with block 1004, and optionally how to concatenate or otherwise combine respective output segments to generate the message.

In accordance with another illustrative embodiment of the present invention, the example rules engine, program code, or processing device can determine that an automatic event should occur (e.g., determine a user should perform a needle prick test), as indicated at blocks 1008 and 1010 in FIG. 10. Accordingly, the example rules engine, program code, or processing device can select the stored message and/or output segments required to provide the user with information about the scheduled event.

As discussed above in connection with FIGS. 9 and 10 and in accordance with example embodiments of the present invention, a number of different types of alarms or selected information are used, for example, as the determined information that a user needs to know and to automatically generate a message, such as:

Abnormal levels: the glucose levels are either above a threshold or below a threshold for a period of time.

Rate of Change: a rate of change exceeds a threshold, indicating that some sort of event occurred (e.g., stress)

Glucose event: the glucose rate of change compared to recent glucose rate of change indicates some sort of action was taken. This may be done to indicate the user consumed a meal, for example, which is useful historical information.

Figure 16:
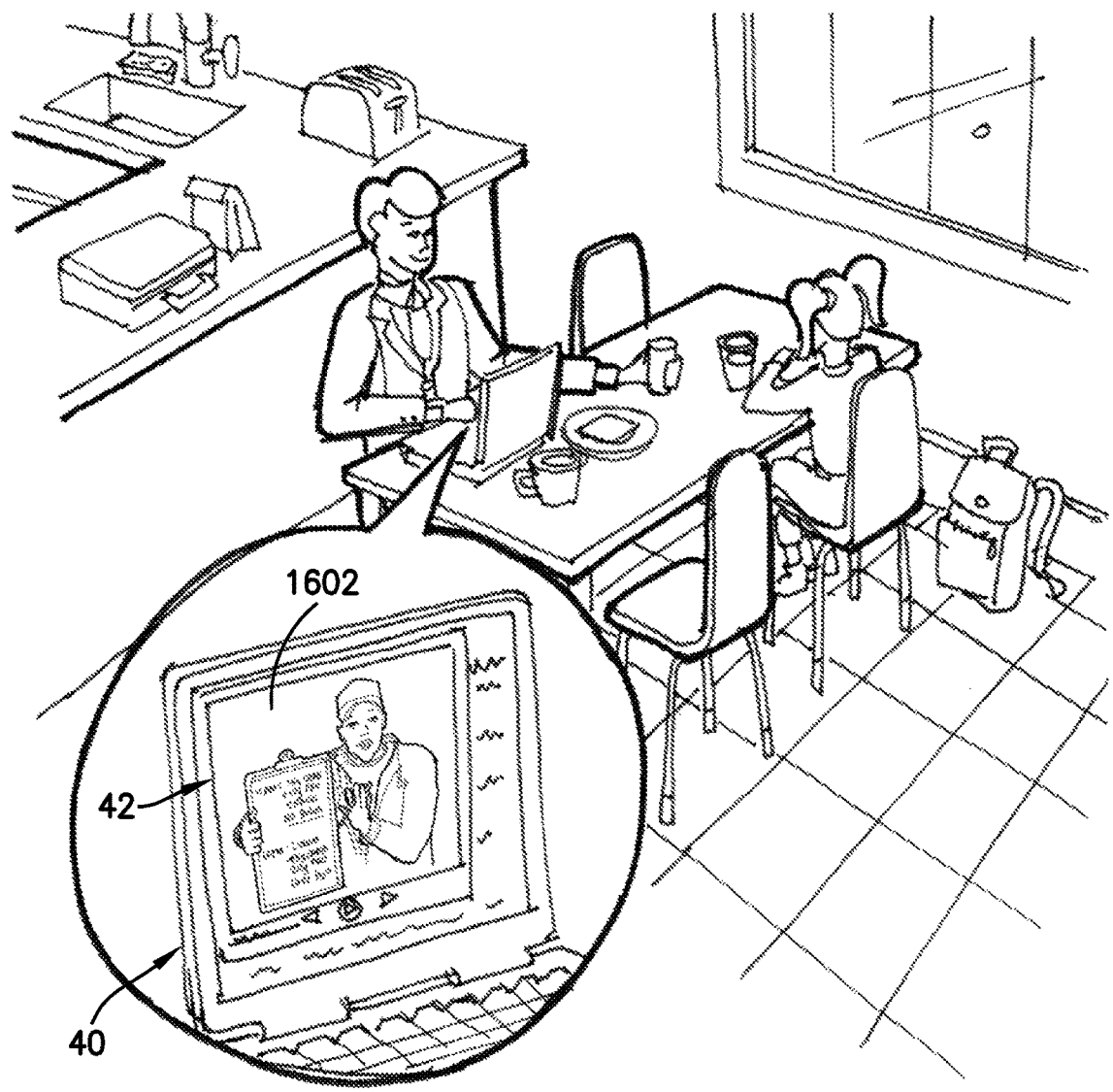
Figure 17:
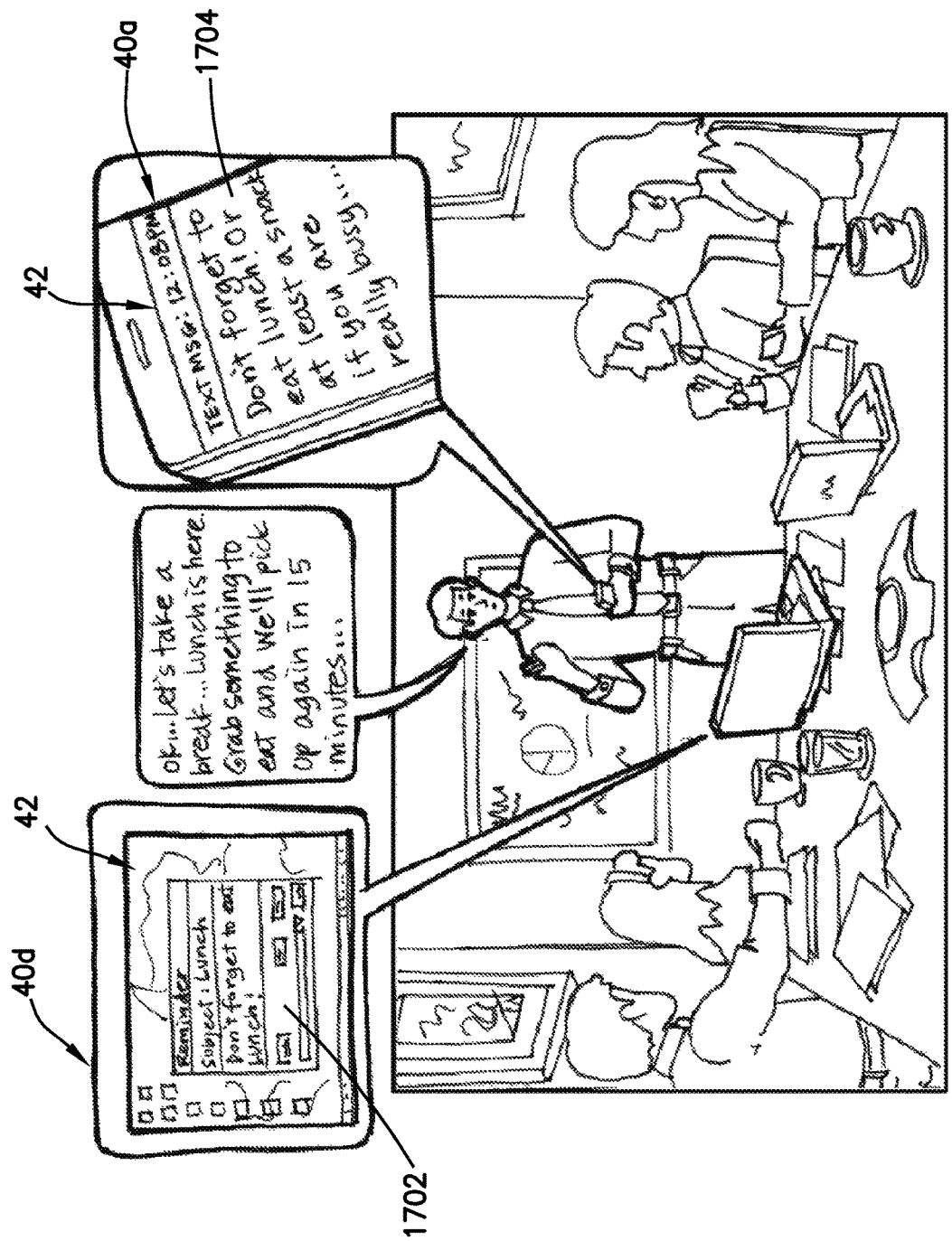

Prospective/Retrospective event: Based on information provided by the user or historical data, the user needs to be aware of a particular pattern of data and/or take corrective action. For example, if the user inputs a 4 hour meeting as part of a daily planner, the system can warn him prior to the meeting that preemptive action may be needed, as illustrated in FIG. 16. In another example, the user may be warned during the meeting that he should take a break, as illustrated in FIG. 17.

Scheduled event: the user of the system scheduled an event (e.g., a needle prick test) to automatically remind the user.

As mentioned above, it is to be understood that other types of information, physiological data criteria and conditions can be selected (e.g., pursuant to a physiological condition management protocol used as the basis to create a rules engine or program code or other processing device) for interpreting inputted data (e.g., measured physiological data 66 and other information 60 such as user configuration data) and determining an output, that is, a message, or a report with which to generate a message, based on combined output segments (e.g., blocks 1002 and 1006) and incorporate evidentiary data (e.g., block 1004).

As mentioned above, example reports, messages or outputted information include, but are not limited to, data highlights or patterns, evidentiary data and optional recommendations for managing the monitored physiological condition in view of the highlighted data, as exemplified in FIGS. 11-19 (e.g., on wrist watch, TV, PC, laptop, mobile phone, PDA, vehicle bus and GUI, among others using text, graphs, video, audio, Outlook™ or other calendar reminders, text messaging, and so on).

Figure 11:
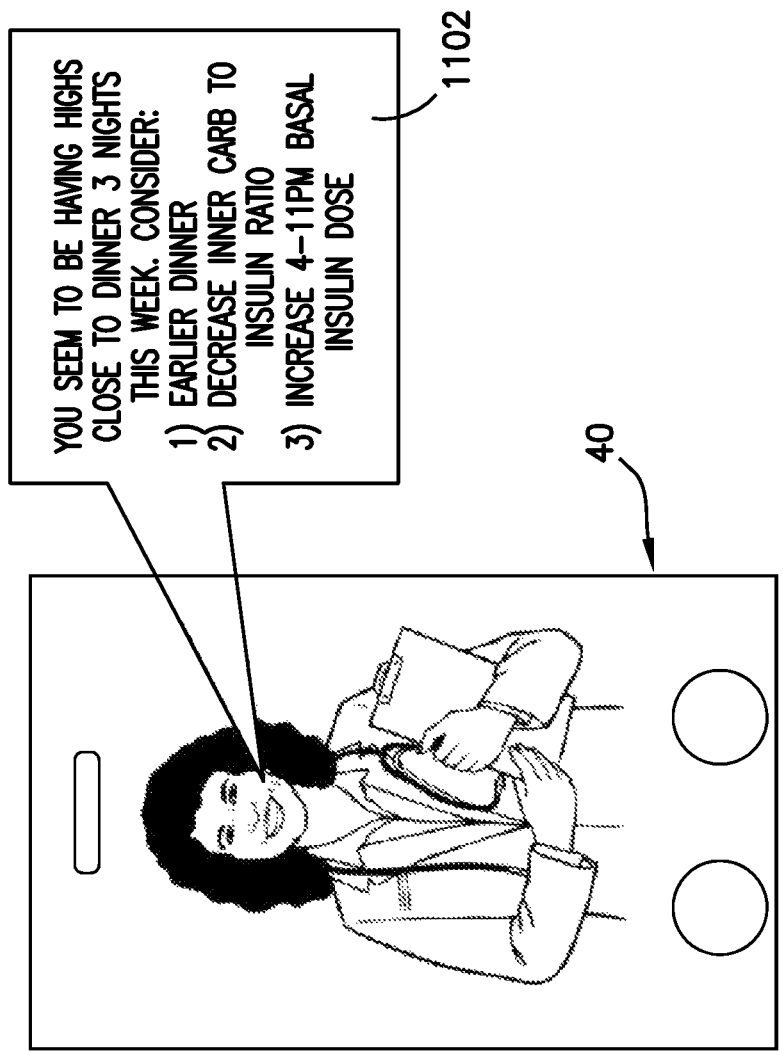
FIGS. 11-19 depict presentations of physiological condition management information in accordance with illustrative embodiments of the present invention.
Figure 13:
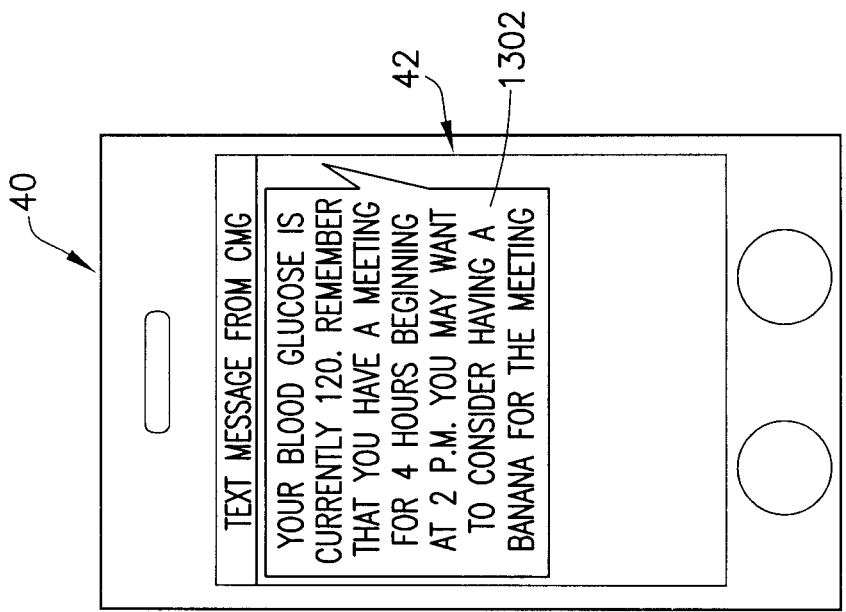
Figure 12:
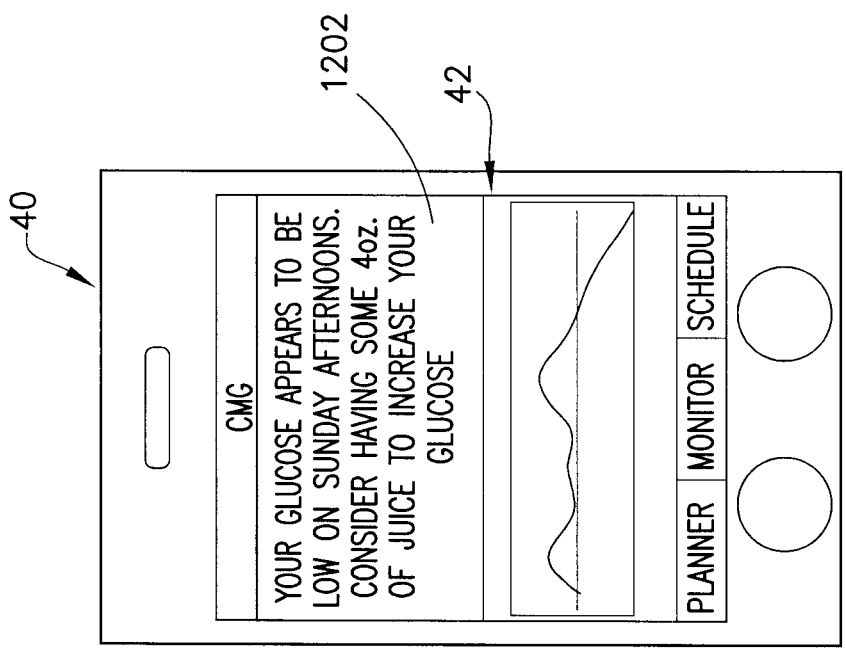

For example, FIGS. 11, 12 and 13 depict a user device 40 configured as a portable device such as a mobile phone or physiological data meter with a video display capability, a graphical display capability and/or a text message display capability, respectively. The user device is programmed or otherwise configured to operate, for example, as described with reference to FIGS. 7-9, that is, to receive measured physiological data 66, store user information 60 and optionally connect to a remote data processing device 36. Based on the measured physiological data 66, user information 60, and reporting parameters 64 (e.g., user configuration data), the user device 40 generates a message (e.g., performs data interpretation and message generation itself as illustrated by blocks 716 and 718) or receives a report from the data processing device 36 with instructions to facilitate generating a message.

FIG. 11 illustrates a user device 40 that plays a video message on a display 42 (e.g., a video or still photo or icon of a coach speaking) with corresponding audio track 1102 played via the device speaker. The message comprises video and audio output segment(s) to generate the interpreted data explanation (e.g., "You seem to be having highs close to X Y days/nights this week" where X is a meal-time such as breakfast, lunch or dinner and Y is an integer, for example), to include the evidentiary data (e.g., where Y is the integer "3" based on a determination of an event that needs to be reported to the user), and to optionally suggest a user action (e.g., "Consider: 1) Earlier dinner. 2) Decrease inner carb to insulin ratio. 3) Increase 4-11 PM Basal insulin dose."). The suggested user action can be determined via the rules engine, for example, based on a protocol such as the above-mentioned SDM, for example. The user device 40 can be configured with controls to replay a message. For example, the generated message can be stored, or temporarily stored, and replayed, for example, in response to a user input to replay within a selected time period after the immediately preceding message delivery. The generated message can be automatically erased after a selected time period, in contrast with the respective output segments that constitute the message, which can remain saved at the user device 40 and/or the data processing device for use in generating other messages.

Similarly, as depicted in FIG. 12, the user device 40 can generate a graphical display with a text message 1202, for example, that has an explanation of a selected event, that is, the processing device in the user device 40 or the data processing device 36 has determined from measured physiological data that the user needs information regarding an event such as a low glucose level during the same time period on each day for a particular day of the week over a period of several weeks such as Sundays, when the user may be finding compliance with a care plan (e.g., eating certain foods at certain times of day and medicating, as prescribed) more difficult than during a weekday (i.e., Monday through Friday).

With reference to FIG. 13, the user device 40 can be programmed to provide the rules engine, or program code or processing device making the determination of information the user needs to know (e.g., block 716, or block 808) with Outlook™ Calendar information of other events that may impact a plan of care for managing a physiological condition. The rules engine, or program code or processing device (e.g., at the user device 40 or the data processing device 36) can combine (e.g., compare) the Outlook™ information with other information relating to the plan of care (e.g., when to deliver medication) and generate a selected message such as the illustrative message 1302. For example, the rules engine, or program code or processing device determines that scheduled meeting on an Outlook™ Calendar may impact a physiological data level that is to be maintained during the meeting time. The current blood glucose, for example, can be calculated to determine a predicted level, as described above in connection with FIG. 9. The message 1302 can be generated to comprise, for example, one or more text output segments relating to reporting current measured physiological data level and event (e.g., as imported from Outlook™ Calendar), incorporated evidentiary data (e.g., level "120"), and a suggested user action (e.g., "having a banana for the meeting").

In accordance with illustrative aspects of the present invention, the selected output segments and/or message can include user-specific adjusted amount(s) of particular action provided by segment according to user data (e.g., get 4 ounces of juice versus 8 ounces). Further, in a clinical setting, the segments can provide highlighted data on a display (e.g., message 1102 can be modified for a health provider to state "patient has been having highs close to dinner for 3 days this week") but also generate backup pages with data (e.g., historical data such as the actual glucose levels measured before and after dinner for each day during the past week) that led to selection of the segments.

Figure 14:
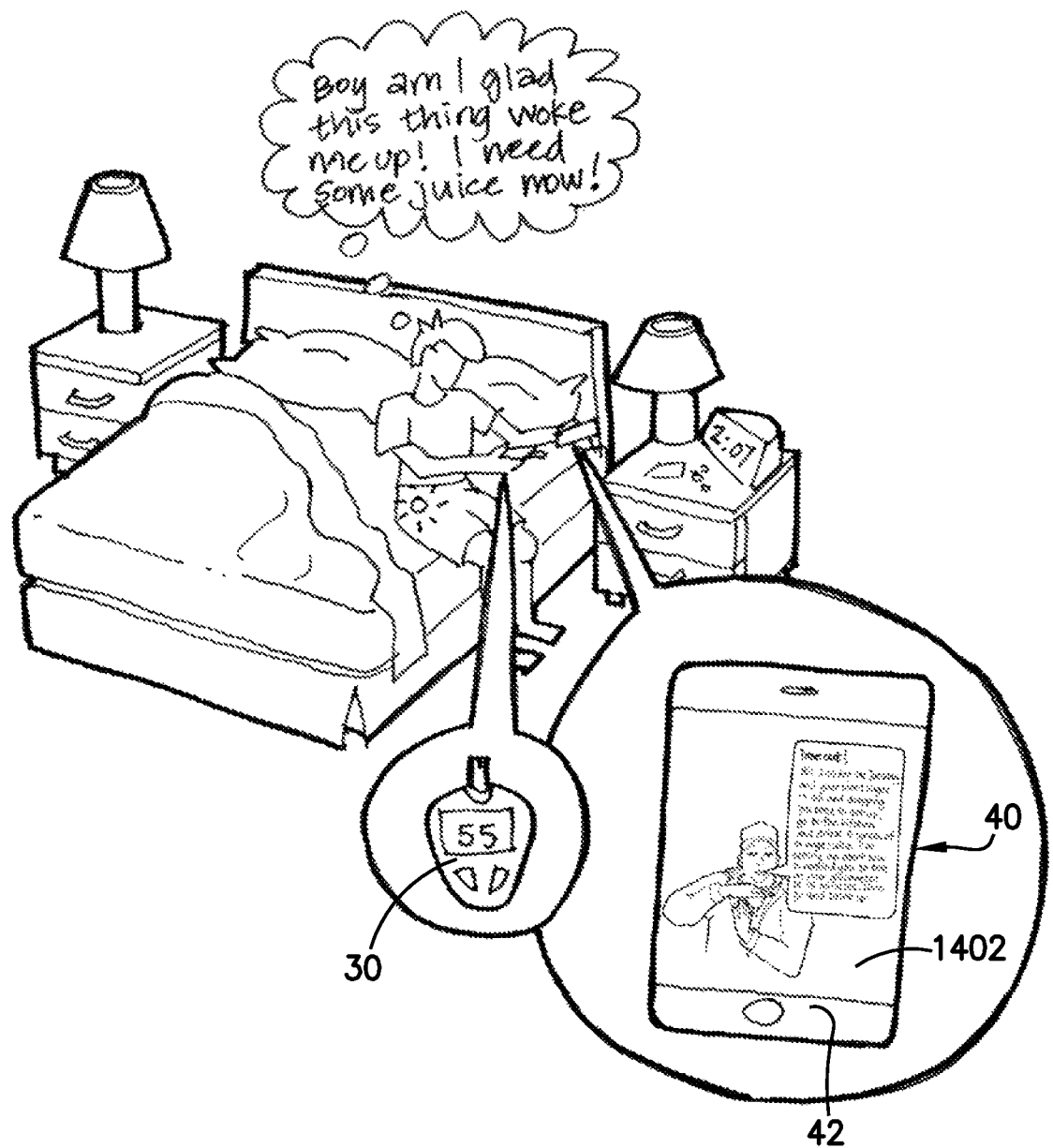

The illustrative user device in FIG. 14 is a mobile phone 40 that is in wireless communication with a continuous glucose monitor (CGM) worn by the patient and indicated at 30. Based on a physiological data received from the CGM 30, the mobile phone 40 generates an alarm message 1402 such as a video with audio track showing a coach (e.g., a coach saying "Time out! It's 2:07 AM on Tuesday and your blood sugar is 62 and dropping. You need to get up, go to the kitchen and drink 8 ounces of orange juice. I'm setting an alert now to remind you to retest on your glucometer in 15 minutes. Now go and drink up!") and setting a retest alarm on the mobile phone. The event that precipitates the alarm message can be determined by the user device (e.g., program code on the mobile phone) or by the data processing device 36 in communication with the mobile phone. The selected message based on the event (e.g., blood sugar dropping below a selected threshold during a selected time period between midnight and 5 AM) can comprise predetermined output segments (e.g., in text, audio, video, or other formats) to explain the event (e.g., "Time out ! It's _____ AM on _____ and your blood sugar is _____ and dropping), with incorporated evidentiary data (e.g., "2:07" AM, on "Tuesday" and glucose level is "62"), and optional predetermined output segments indicating recommended user action (e.g., "You need to get up, go to the kitchen and drink 8 ounces of orange juice. I'm setting an alert now to remind you to retest on your glucometer in 15 minutes. Now go and drink up!"). The recommendation can be based, for example, on a selected physiological condition management protocol used for the rules engine (e.g., SDM) or other program code or processing device configured to determine what information (e.g., events and message components) a user needs to know based on measured physiological data and other information.

Figure 15:
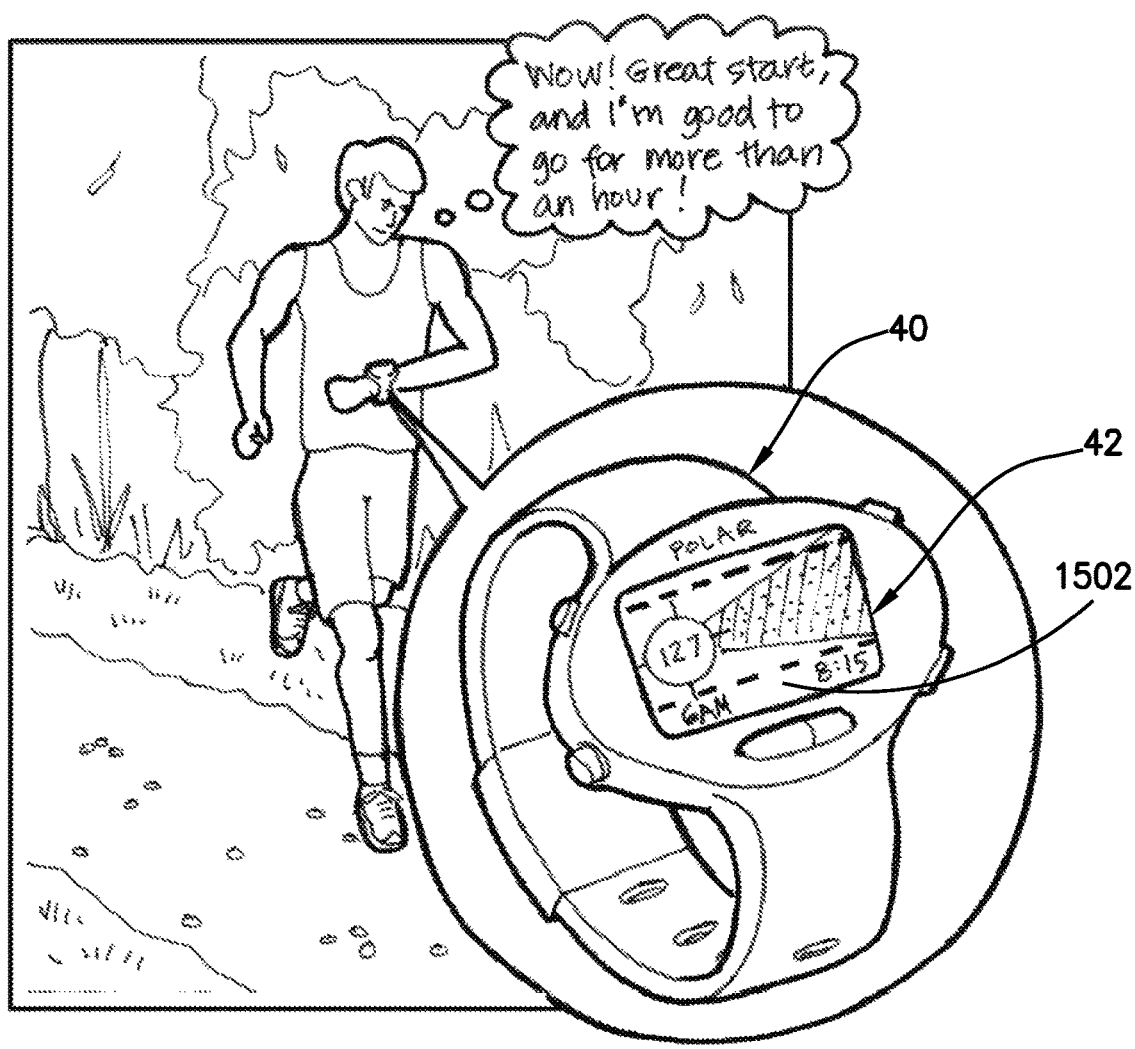

In accordance with another illustrative embodiment of the present invention, a user device 40 can be a wearable exercise device such as a watch, for example, as shown in FIG. 15. When a patient with a monitored physiological condition goes on a morning run, he may not know how long his blood glucose is going to stay stable during the exercise. With a conventional glucometer, he can watch his currently measured number and how it is trending, but he may have to stop often to check his blood glucose with his glucometer to know with certainty, and then he will have to think about what to do when he gets the glucometer outputted number. Thus, he has difficulty completing a full workout with a conventional glucometer without stopping to manage his diabetes.

The user device 40 illustrated in FIG. 15 is advantageous because, when the patient goes for his morning run, he can just glance at his watch 40. The user device watch 40 links (e.g., wirelessly) to his CGM and will show him a predictive graph 1502 (e.g., in accordance with processing described in connection with block 908) that tells him not only what his blood glucose is now, but how long in his current activity state that his blood glucose will remain stable. Thus, he can do his whole workout with confidence and without interruptions to manage his diabetes The user device 40 (e.g., a laptop) in FIG. 16 coordinates event and message determination with Outlook™ Calendar appointments and generates a message of a coach providing a plan for managing a physiological condition (e.g., diabetes) throughout particular day in accordance with the Outlook™ schedule for the day in accordance with an illustrative embodiment of the present invention. With a conventional glucometer that is not operating with Outlook, a user checks his day's schedule and emails at breakfast and realizes what challenges or physiological condition triggers he must endure for the day. He may have a negative feeling that an earlier run that morning is going to drop his blood sugar at some point during the day. He hopes that this drop does not occur in the middle of a meeting, which would leave him looking unprepared since he knows he cannot think clearly when his blood sugar is low.

The user device 40 (e.g., a laptop) depicted in FIG. 16 is advantageous because it can determine an event (e.g., a morning glucose reading predicted to drop during a scheduled meeting without food intake) and generate a video message for playback in the morning at breakfast (e.g., a video of a coach providing a plan for the day) so that the user knows what he needs to eat and when to keep his blood glucose on target. He can plan it into his schedule so that his day goes more smoothly.

The user devices 40*d* and 40*a* in FIG. 17 depict generation of a message concurrently on different types of user devices, that is, a laptop and a mobile phone (e.g., that is wirelessly linked to a CGM) in accordance with illustrative embodiments of the present invention. The user configuration data 60 and/or the reporting rules 64 or other user information can be used to control the rules engine, program code, or processing device at the user device 40 and/or the data processing device 36 to determine what information a user needs to know (e.g., an event such as a morning glucose reading can be predicted to drop during a scheduled meeting without food intake), a message (e.g., a prerecorded reminder) and message format (e.g., based on a user preference) such as a text message on the mobile phone 40a and a text reminder in an Outlook™ Calendar meeting reminder.

A conventional glucometer is disadvantageous in situations where, for example, its 12:45 PM and the user has been in a meeting since 10 AM and is late getting lunch. When his CGM starts alarming, he may be self-conscious about his alarm advertising to his colleagues that he is having a medical issue, and having to take a break that was not planned to manage the issue. The user devices 40d and 40a depicted in FIG. 17 are advantageous over the conventional glucometer in that his mobile phone 40a can be configured in accordance with illustrative embodiments of the present invention to generate a text message 1704 (e.g., using a special, unobtrusive tone that is designated to be an alarm to avoid a hypoglycemic event) such as a reminder to take a break to manage his physiological condition. By using a tone and predictive and/or scheduled operations of the user device 40a, and not relying on a CGM alarm, the user can arrange for a meeting break and discreetly manage his condition. A similar discreet and advance reminder message 1702 can also be generated on his laptop and allow him to take a planned break on his terms so the flow of his meeting is not interrupted by anything unexpected and he can maintain control of his presentation.

The user device 40 in FIG. 17 depicts generation of a message on a television or PC monitor in accordance with illustrative embodiments of the present invention. Conventional CGMs can provide a user with significant amounts of blood glucose level data such as measured levels over various periods of time indicated as charts or bar graphs in a graphical display on a computer or TV screen. Conventional graphical displays of measured physiological data, however, are disadvantageous since they are difficult to read or interpret. For example, a user can find that, at 9:15 PM (e.g., when he is finally home after a long day at work and eating dinner entirely too late for the third night in a week), that his blood glucose numbers are not on target for his prescribed plan of care. Further, he may be too tired to look at all of the charts provided by the CGM or may not even understand them. Such a user may have to make an appointment with his endocrinologist to seek help with the necessary corrections before he can get his blood glucose levels back on target.

Figure 18:
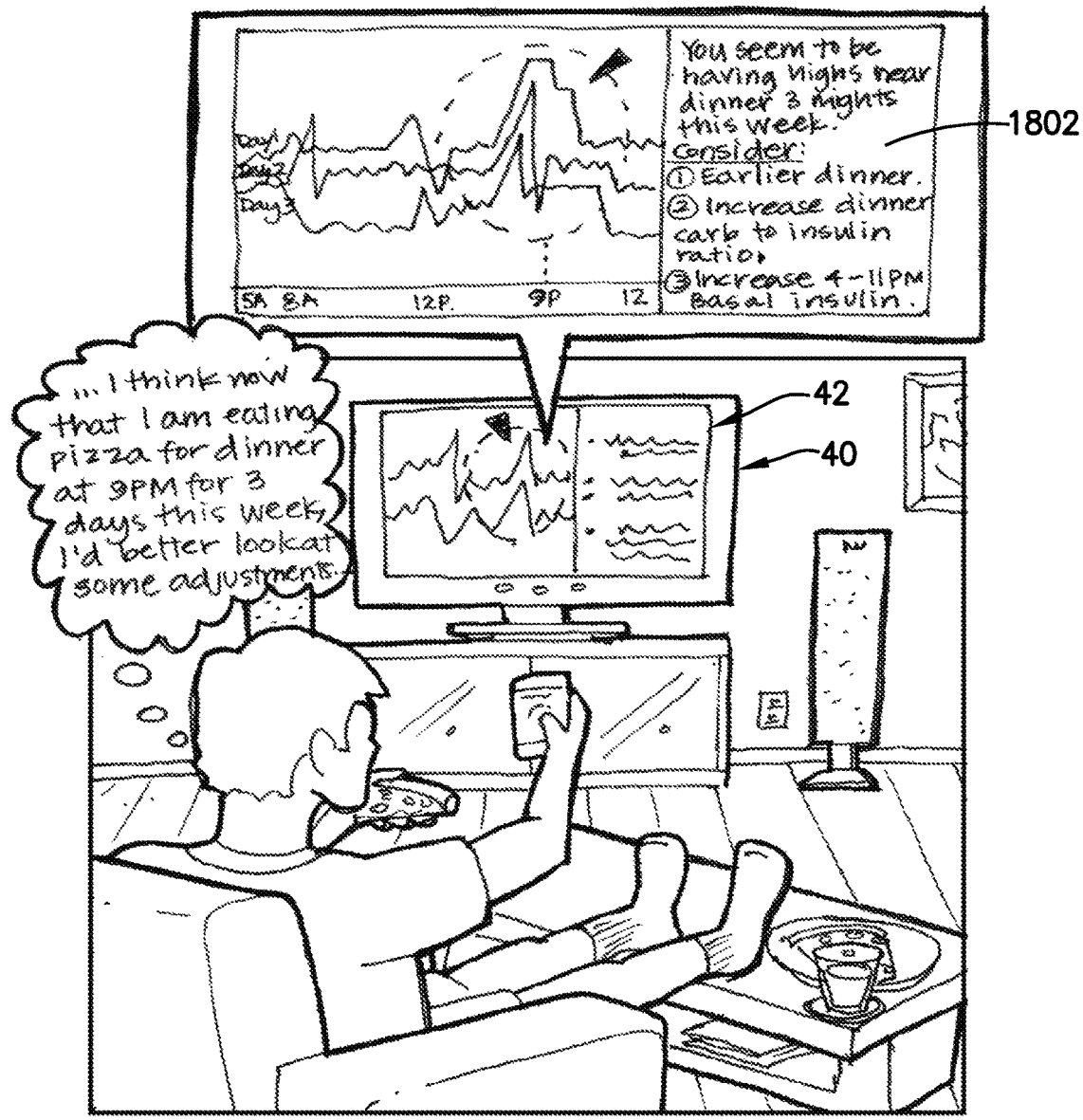

The user device 40 in FIG. 18 is advantageous because it is configured to simply automatically determine information the user needs to know such as an event(s) (e.g., target blood glucose levels out of range over the entire week and particularly off target by a larger degree at night), the user behaviors that may be contributing to the event(s) (e.g., late dinners, carbohydrate intake, administered medication amounts and times) and generate a message 1802 with recommendations based on the users inputted behaviors of user corrective behavior. A message such as the message 1802 displayed on a screen 42 in FIG. 18 does not overwhelm the user with unnecessary information as would charts provided by conventional devices. Further, the user device 40 in FIG. 18 permits the user to understand cause effect relationships between his behavior and monitored physiological data.

Figure 19:
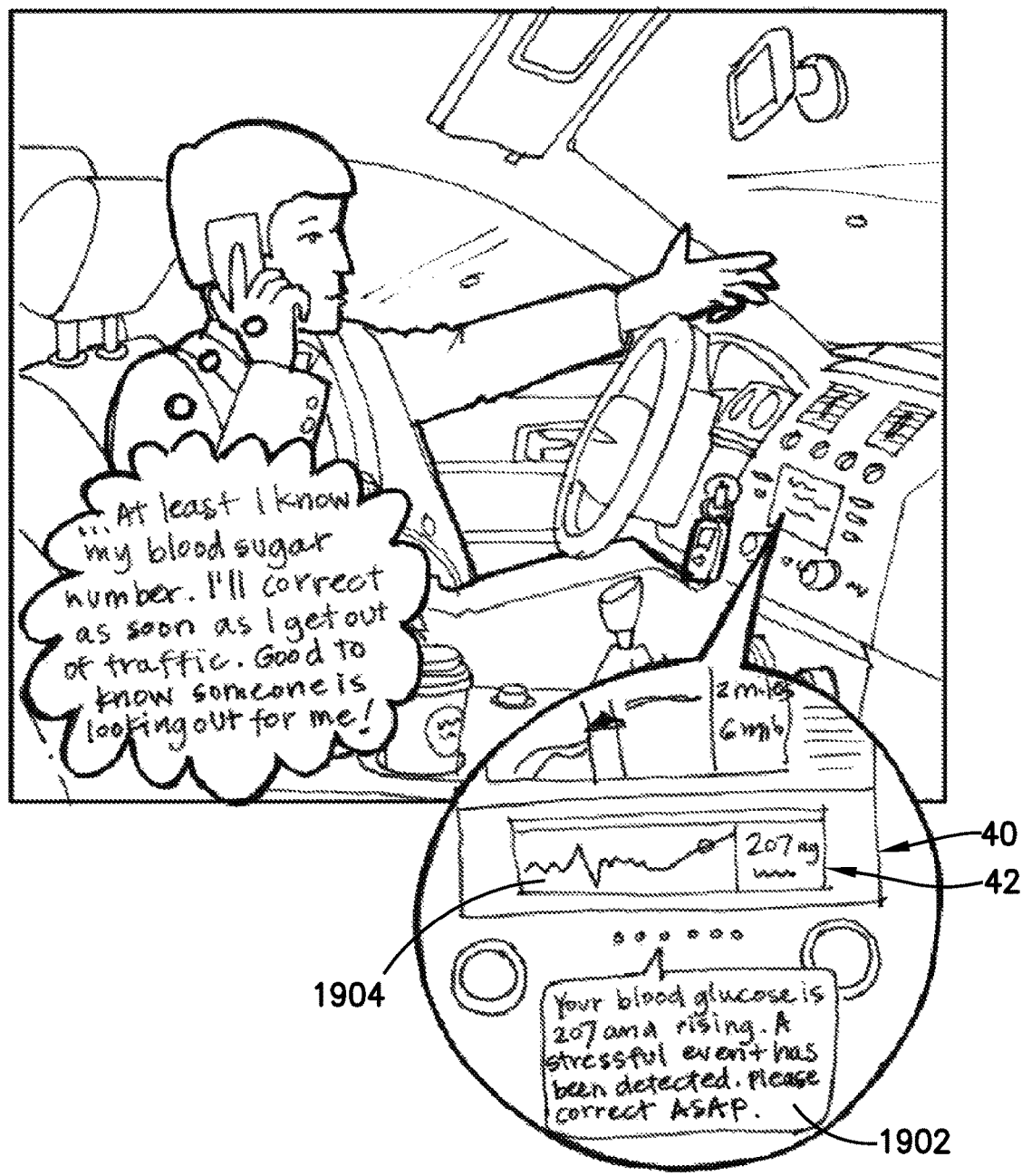

The user device 40 in FIG. 19 depicts generation of a message on a vehicle user interface in accordance with illustrative embodiments of the present invention. When a patient wearing a CGM is driving, it can be difficult to manage his diabetes when he is detained by traffic congestion. For example, it may be difficult for the user to stop driving to check his CGM to see what his blood sugar is doing. In addition to being stressed because he is driving in heavy traffic, he may be further stressed by not knowing his current CGM reading or what his stress level will do to his blood glucose levels. Depending on the amount of time he is detained in traffic, he may not be able to take corrective actions as needed to mitigate a hypoglycemic event.

The vehicle-based user device 40 in FIG. 19 is advantageous because it allows a driver convenient access to his current blood glucose reading and can provide a message 1902 such as an observation of an event (e.g., based on a predicted level) and optionally detected stressors or triggers (e.g., erratic pulmonary function, increased heart rate, vehicle sensors such as accelerometers or trip meters indicating excessive slowness or breaking) and a reminder to manage his condition.

Illustrative embodiments of the present invention can be implemented, at least in part, in digital electronic circuitry, analog electronic circuitry, or in computer hardware, firmware, software, or in combinations of them. The components of the user devices 40 and data processing device 36 can be implemented as a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Illustrative embodiments of the present invention have been described with reference to a programmed physiological sensor, monitor, rules engine, server, among other components. It is to be understood, however, that the present invention can also be embodied as computer-readable codes on a computer-readable recording medium. The computer-readable recording medium is any data storage device that can store data which can thereafter be read by a computer system. Examples of the computer-readable recording medium include, but are not limited to, read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion.

Also, functional programs, codes, and code segments for accomplishing the present invention can be easily construed as within the scope of the invention by programmers skilled in the art to which the present invention pertains.

Method steps, processes or operations associated with a user device 40 or data processing device 36 can be performed by one or more programmable processors executing a computer program to perform functions of the invention by operating on input data and generating an output. Method steps can also be performed by, and an apparatus according to illustrative embodiments of the present invention, can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

While the invention herein disclosed has been described by means of specific embodiments and applications thereof, numerous modifications and variations can be made thereto by those skilled in the art without departing from the scope of the invention.

What is claimed is:

1. A method of generating physiological condition information comprising:
    coupling to at least one physiological condition sensor to receive measured physiological data corresponding to a user therefrom;
    storing the physiological data and user information in a memory device, the user information selected from the group consisting of physiological data thresholds, meal times, exercise times, age, weight, medication, amounts and times of medication administration, heart rate, body temperature, and food intake information;
    analyzing, via a processing device comprising a rules engine, the physiological data to determine whether an event relating to the physiological data has occurred or will occur and for which the user is to be alerted, the event represented by event information that is selected for the user and that is determined via the processing device using a rules engine and a designated protocol for managing the physiological condition, the physiological data, and at least one of the user information, the event information comprising at least one of a selected data point and a selected pattern of the physiological data that indicates at least one of a rate of change in the physiological data that exceeds a designated threshold, a predicted value corresponding to the physiological data, and physiological data failing to meet designated parameters during a designated time period on each of a plurality of days; and
    when the processing device determines the user is to be alerted of an event, generating, via the processing device, a presentation of physiological condition information that comprises a video, the video presenting an explanation of the event information that includes at least one of values selected from among the stored physiological data and the stored user information that contributed to the event information, and values derived from at least one of the stored physiological data and the stored user information that contributed to the event information.

2. A method as claimed in claim 1, further comprising storing a plurality of output segments in the memory device that are predetermined and stored independently of the received physiological data, wherein the output segments are at least one of audio segments and video segments, and the generating comprises selecting and combining selected ones of the output segments to create the video.

3. A method as claimed in claim 1, wherein the presentation can comprise at least one of an audio output, a graphical output, an audiovisual output, and an alphanumeric output.

4. A method as claimed in claim 1, further comprising storing a plurality of output segments in the memory device that are predetermined and stored independently of the received physiological data, the stored output segments being at least one of audio, video and audiovisual, wherein generating comprises selecting and combining selected ones of the output segments to create the presentation.

5. A method as claimed in claim 4, wherein the output segments are recordings of user instructions for performing at least part of a physiological condition management action, and the analyzing comprises selecting one of a plurality of physiological condition management actions.

6. A method as claimed in claim 2, wherein the output segments are at least one of video recordings, audio recordings and graphical representations of a person or character presenting at least part of the presentation.

7. A method as claimed in claim 2, wherein the combining selected ones of the output segments comprises at least one of concatenating the selected ones of the output segments, overlaying the selected ones of the output segments, splicing the selected ones of the output segments into one another or into a separate stream, and outputting the selected ones of the output segments in respective positions in an output display screen.

8. A method as claimed in claim 2, wherein the generating comprises at least one of inserting the values among the combined output segments, simultaneously displaying the values in at least one of the combined segments, and combining the values with the combined output segments.

9. A method as claimed in claim 1 further comprising:
    storing in a memory device a plurality of output segments that are predetermined and based on a designated protocol for managing the physiological condition, the stored output segments being at least one of audio, video, graphical, alphanumeric and audiovisual content;
    wherein the generating comprises generating, via the processing device, a presentation of physiological condition information that is selected based on the designated protocol and comprises an explanation of the determined pattern or selected data point based on the designated protocol by combining selected ones of the output segments to create the presentation.

10. A method as claimed in claim 9, further comprising inserting values among the combined output segments, the values being at least one of values selected from among the stored physiological data and the stored user information that contributed to the determined pattern, and values derived from at least one of the stored physiological data and the stored user information that contributed to the determined pattern.

11. A method as claimed in claim 10, wherein the predetermined output segments are at least parts of instructions for user actions to perform at least part of the designated protocol for managing a physiological condition in a user having the determined pattern or selected data point.

12. An apparatus for generating physiological condition information comprising:

a communication link for coupling with at least one physiological condition sensor to receive measured physiological data corresponding to a user therefrom;

a memory device for storing
- a plurality of output segments that are predetermined and based on a designated protocol for managing the physiological condition, the stored output segments being at least one of audio, video, graphical, alphanumeric and audiovisual content, and
- physiological data and user information corresponding to a user, the user information selected from the group consisting of physiological data thresholds, meal times, exercise times, age, weight, medication, amounts and times of medication administration, heart rate, body temperature, and food intake information; and a processing device connected to the memory device and configured to
- analyze the physiological data to determine whether an event relating to the physiological data has occurred or will occur and for which the user is to be alerted, the event being represented by event information that is selected for the user and that is determined via the processing device using a rules engine based on the designated protocol, the physiological data, and at least one of the user information and protocol data for managing the physiological condition, the event information comprising at least one of a selected data point and a selected pattern of the physiological data that indicates at least one of a rate of change in the physiological data that exceeds a designated threshold, a predicted value corresponding to the physiological data, and physiological data failing to meet designated parameters during a designated time period on each of a plurality of days, and
- when the processing device determines the user is to be alerted of an event, generate a presentation of physiological condition information that is selected based on the designated protocol and comprises an explanation of the event information by combining selected ones of the output segments and the selected event information to create the presentation.

13. An apparatus as claimed in claim 12, wherein the processing device is further configured to insert values among the combined output segments, the values being at least one of values selected from among the stored physiological data and the stored user information that contributed to the determined pattern, and values derived from at least one of the stored physiological data and the stored user information that contributed to the determined pattern.

14. An apparatus as claimed in claim 13, wherein the predetermined output segments are at least parts of instructions for performing at least part of the designated protocol for managing a physiological condition in a user having the determined pattern or selected data point.

15. An apparatus as claimed in claim 14, wherein the processing device, using the rules engine, determines the physiological condition information selected for the presentation based on the designated protocol.

16. A method as claimed in claim 1 wherein the physiological condition and the physiological data are related to glycemic control.

17. A method as claimed in claim 1 wherein the physiological data are measured subcutaneously or intravenously.

18. A method as claimed in claim 1, wherein receiving the physiological data comprises:
- inductively coupling, via an inductive link, a sensor deployed in the user with an external user device;
- powering the sensor via the inductive link; and
- performing initial pairing of the sensor and the user device.

19. A method as claimed in claim 18, wherein performing initial pairing comprises exchanging security information.

20. A method as claimed in claim 18, wherein powering the sensor comprises using a quasi-static H field.

21. A method as claimed in claim 1, wherein the analyzing further comprises determining that an event will not occur based on the predicted value, and the presentation comprises a confirmation message indicating that the event will not occur.

22. A method as claimed in claim 1, wherein the analyzing comprises comparing the physiological data to a user computer calendar and determining a time period on the calendar during which an event is predicted to occur, and the presentation comprises a suggested user action to be taken during the time period to mitigate or avoid the effects of the event.

23. The method as claimed in claim 1, wherein the coupling to at least one sensor and receiving physiological data corresponding to a user therefrom comprises receiving streams of the physiological data wirelessly from the at least one sensor, and the analyzing, via the processing device, comprises analyzing the received streams of the physiological data.

24. The method as claimed in claim 23, wherein the coupling to at least one sensor and receiving physiological data corresponding to a user therefrom comprises receiving streams of the physiological data wirelessly from a plurality of sensors, and the analyzing, via the processing device, comprises analyzing the received streams of the physiological data.

25. A method as claimed in claim 1, wherein the storing comprises also storing at least one of environmental, stressor and trigger data in the memory device, and the video comprises suggestive recommendations to the user to manage the monitored physiological condition associated with the at least one of environmental, stressor and trigger data.

26. A method as claimed in claim 1, wherein the video comprises instructions for user actions to perform at least part of the designated protocol for managing the physiological condition in a user.

27. A method as claimed in claim 26, wherein the instructions are different according to an intended recipient operator of a user device.

28. An apparatus as claimed in claim 12, wherein memory device also stores at least one of environmental, stressor and trigger data in the memory device, and the output segments of the presentation comprises suggestive recommendations to the user to manage the monitored physiological condition associated with the at least one of environmental, stressor and trigger data.

29. An apparatus as claimed in claim 12, wherein the output segments of the presentation comprise instructions for user actions to perform at least part of the designated protocol for managing the physiological condition in a user.

30. An apparatus as claimed in claim 29, wherein the instructions are different according to an intended recipient operator of a user device.

* * * * *